US008586708B2

(12) United States Patent
Ting et al.

(10) Patent No.: US 8,586,708 B2
(45) Date of Patent: Nov. 19, 2013

(54) MONOVALENT STREPTAVIDIN COMPOSITIONS

(75) Inventors: Alice Y. Ting, Cambridge, MA (US); Mark R. Howarth, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/262,325

(22) Filed: Oct. 28, 2005

(65) Prior Publication Data

US 2007/0099248 A1 May 3, 2007

(51) Int. Cl.
*C07K 14/36* (2006.01)
*C07K 1/02* (2006.01)
*C07K 1/13* (2006.01)
*G01N 33/68* (2006.01)

(52) U.S. Cl.
USPC ............. 530/350; 435/7.4; 435/7.6; 530/412; 530/427

(58) Field of Classification Search
USPC .............................................. 435/4
See application file for complete search history.

(56) References Cited

U.S. PATENT DOCUMENTS

| 6,156,493 | A | 12/2000 | Stayton |
|---|---|---|---|
| 2004/0209317 | A1 | 10/2004 | Ting |
| 2004/0265906 | A1 | 12/2004 | Ting |
| 2005/0233389 | A1 | 10/2005 | Ting et al. |
| 2007/0105162 | A1 | 5/2007 | Ting et al. |

OTHER PUBLICATIONS

Freitag, S., et al. 1999 Biomolecular Engineering 16: 13-19.*
Yasugi, M., et al. 2001 Protein Engineering 14(8): 601-607.*
Wells, J.A., et al. 1990 Biochemistry 29(37): 8509-8517.*
Aslan, F.M. et al., Engineered single-chain dimeric streptavidins with an unexpected strong preference for biotin-4-fluorescein. Proc Natl Acad Sci U S A. 102(24): 8507-8512, 2005.
Avrantinis, S.K. et la., Dissecting the streptavidin-biotin interaction by phage-displayed shotgun scanning. Chembiochem. 3(12): 1229-1234, 2002.
Bayer, E.A. et al., Sodium dodecyl sulfate-polyacrylamide gel electrophoretic method for assessing the quaternary state and comparative thermostability of avidin and streptavidin. Electrophoresis 17: 1319-1324, 1996.
Bittker, J.A. et al., Nucleic acid evolution and minimization by nonhomologous random recombination. Nat. Biotechnol. 20, 1024-1029, 2002.
Chen, I. and Ting, A.Y. Site-specific labeling of proteins with small molecules in live cells. Curr. Opin. Biotechnol. 16, 35-40, 2005.
Chen, I. et al., Site-specific labeling of cell surface proteins with biophysical probes using biotin ligase. Nat Methods 2: 99-104, 2005.
Chilkoti, A. et al., Engineered chimeric streptavidin tetramers as novel tools for bioseparations and drug delivery. Biotechnology (N Y). 13(11):1198-1204, 1995.

Chilkoti, A. et al., Site-directed mutagenesis studies of the high-affinity streptavidin-biotin complex: contributions of tryptophan residues 79, 108, and 120. Proc. Natl. Acad. Sci. U. S. A 92, 1754-1758, 1995.
Chu, V. et al., Thermodynamic and structural consequences of flexible loop deletion by circular permutation in the streptavidin-biotin system. Protein Sci. 7(4): 848-859, 1998.
Coleman, T.M. and Huang, F. RNA-catalyzed thioester synthesis. Chem Biol 9: 1227-1236, 2002.
Graf, E.R. et al., Neurexins induce differentiation of GABA and glutamate postsynaptic specializations via neuroligins. Cell 119: 1013-1026, 2004.
Green, N.M. and Toms, E.J. The properties of subunits of avidin coupled to sepharose. Biochem. J. 133: 687-700, 1973.
Green, N.M. Avidin and streptavidin. Methods Enzymol. 184: 51-67, 1990.
Hamblett, K.J. et al., A streptavidin-biotin binding system that minimizes blocking by endogenous biotin. Bioconjug Chem. 13(3): 588-598, 2002.
Holmberg, A. et al., The biotin-streptavidin interaction can be reversibly broken using water at elevated temperatures. Electrophoresis. 26(3): 501-510, 2005.
Howarth, M. et al., Targeting quantum dots to surface proteins in living cells with biotin ligase. Proc. Natl. Acad. Sci. U. S. A 102: 7583-7588, 2005.
Hyre, D.E. et al., Ser45 plays an important role in managing both the equilibrium and transition state energetics of the streptavidin-biotin system. Protein Sci. 9, 878-885, 2000.
Iino, R. et al., Single molecule imaging of green fluorescent proteins in living cells: E-cadherin forms oligomers on the free cell surface. Biophys J. 80(6): 2667-2677, 2001.
Kada, G. et al., Accurate measurement of avidin and streptavidin in crude biofluids with a new, optimized biotin-fluorescein conjugate. Biochim Biophys Acta 1427: 33-43, 1999.
Keefe, A.D. et al., One-step purification of recombinant proteins using a nanomolar-affinity streptavidin-binding peptide, the SBP-Tag. Protein Expr.Purif. 23(3), 440-446. 2001.
Klemm, J.D. et al., Dimerization as a regulatory mechanism in signal transduction. Annu. Rev. Immunol. 16, 569-592, 1998.
Klumb, L.A. et al., Energetic roles of hydrogen bonds at the ureido oxygen binding pocket in the streptavidin-biotin complex. Biochemistry 37, 7657-7663, 1998.
Laitinen, O.H. et al. Rational design of an active avidin monomer. J. Biol. Chem. 278, 4010-4014, 2003.
Lamla, T. and Erdmann, V.A. The Nano-tag, a streptavidin-binding peptide for the purification and detection of recombinant proteins. Protein Expr.Purif. 33(1), 39-47, 2004.

(Continued)

*Primary Examiner* — Marsha Tsay
(74) *Attorney, Agent, or Firm* — Wolf, Greenfield & Sacks, P.C.

(57) ABSTRACT

The invention relates, in part, to monovalent streptavidin compositions. The invention also relates to methods of preparing and using monovalent streptavidin compositions. In some aspects of the invention, the compositions are monovalent streptavidin with a single femtomolar biotin-binding site.

14 Claims, 5 Drawing Sheets

(56) References Cited

OTHER PUBLICATIONS

Levinson, J.N. et al. Neuroligins mediate excitatory and inhibitory synapse formation: involvement of PSD-95 and neurexin-1beta in neuroligin-induced synaptic specificity. J. Biol. Chem. 280, 17312-17319, 2005.

Nordlund, H.R. et al., Tetravalent single chain avidin: From subunits to protein domains via circularly permuted avidins. Biochem J. 2005.

Pazy, Y. et al., Ligand exchange between proteins. Exchange of biotin and biotin derivatives between avidin and streptavidin. J Biol Chem. 277(34): 30892-30900, 2002.

Prange, O. et al., A balance between excitatory and inhibitory synapses is controlled by PSD-95 and neuroligin. Proc. Natl. Acad. Sci. U. S. A 101, 13915-13920, 2004.

Qureshi, M.H., et al., Development and characterization of a series of soluble tetrameric and monomeric streptavidin muteins with differential biotin binding affinities. J. Biol. Chem. 276, 46422-46428, 2001.

Rathbone, M.P. et al., Trophic effects of purines in neurons and glial cells. Prog Neurobiol 59: 663-690, 1999.

Reznik, G.O. et al., A streptavidin mutant with altered ligand-binding specificity. Proc. Natl. Acad. Sci. U. S. A 95: 13525-13530, 1998.

Reznik, G.O. et al., Streptavidins with intersubunit crosslinks have enhanced stability. Nat Biotechnol. 14(8): 1007-1011, 1996.

Sano, T. & Cantor, C.R. Intersubunit contacts made by tryptophan 120 with biotin are essential for both strong biotin binding and biotin-induced tighter subunit association of streptavidin. Proc. Natl. Acad. Sci. U. S. A 92: 3180-3184, 1995.

Sano, T. and Cantor, C.R., Expression of a cloned streptavidin gene in *Escherichia coli*. Proc Natl Acad Sci USA 87: 142-146, 1990.

Sano, T. et al., Recombinant core streptavidins. A minimum-sized core streptavidin has enhanced structural stability and higher accessibility to biotinylated macromolecules. J Biol Chem. 270(47): 28204-9, 1995.

Scheiffele, P. et al., Neuroligin expressed in nonneuronal cells triggers presynaptic development in contacting axons. Cell 101: 657-669, 2000.

Schmidt, T.G. and Skerra, A. One-step affinity purification of bacterially produced proteins by means of the "Strep tag" and immobilized recombinant core streptavidin. J. Chromatogr. A 676: 337-345, 1994.

Schwartz, B.L. et al., Dissociation of tetrameric ions of noncovalent streptavidin complexes formed by the eletrospray-ionization. J. of Aner. Soc. for Mass Spec. 6: 459-465, 1995.

Srisawat, C. and Engelke, D.R. Streptavidin aptamers: affinity tags for the study of RNAs and ribonucleoproteins. RNA. 7, 632-641, 2001.

Wong, J. et al., Direct force measurements of the streptavidin-biotin interaction. Biomol Eng. 16(1-4): 45-55, 1999.

Wu, S.C. and Wong, S.L. Engineering soluble monomeric streptavidin with reversible biotin binding capability. J. Biol. Chem. 280, 23225-23231, 2005.

Airenne, K.J., Recombinant avidin and avidin-fusion proteins, Biomol Eng. Dec. 31, 1999;16(1-4):87-92.

Jarvik, J.W. and Telmer, C.A., Epitope tagging, Annu Rev Genet. 1998;32:601-18.

Laintinen, O.H., Biotin induces tetramerization of a recombinant monomeric avidin. A model for protein-protein interactions. J Biol Chem. Mar. 16, 2001;276(11);9219-24. Epub Nov. 13, 2000.

Muzykantov, V.R., et al, Regulation of the complement-mediated elimination of red blood cells modified with biotin and streptavidin, Anal Biochem. Oct. 1, 1996;241(1):109-19.

Midlvan, A.S. et al., Quantitative interpretations of double mutations of enzymes. Arch Biochem Biophys. May 1, 1992;294(2):327-40. Review. Erratum in: Arch Biochem Biophys Aug. 15, 1992;297(1):188.

\* cited by examiner

Magnification of lower part of graph

SEQUENCE LISTING

```
<160> NUMBER OF SEQ ID NOS: 15

<210> SEQ ID NO 1
<211> LENGTH: 183
<212> TYPE: PRT
<213> ORGANISM: Streptomyces avidinii

<400> SEQUENCE: 1

Met Arg Lys Ile Val Val Ala Ala Ile Ala Val Ser Leu Thr Thr Val
1               5                   10                  15

Ser Ile Thr Ala Ser Ala Ser Ala Asp Pro Ser Lys Asp Ser Lys Ala
                20                  25                  30

Gln Val Ser Ala Ala Glu Ala Gly Ile Thr Gly Thr Trp Tyr Asn Gln
            35                  40                  45

Leu Gly Ser Thr Phe Ile Val Thr Ala Gly Ala Asp Gly Ala Leu Thr
        50                  55                  60

Gly Thr Tyr Glu Ser Ala Val Gly Asn Ala Glu Ser Arg Tyr Val Leu
65                  70                  75                  80

Thr Gly Arg Tyr Asp Ser Ala Pro Ala Thr Asp Gly Ser Gly Thr Ala
                85                  90                  95

Leu Gly Trp Thr Val Ala Trp Lys Asn Asn Tyr Arg Asn Ala His Ser
            100                 105                 110

Ala Thr Thr Trp Ser Gly Gln Tyr Val Gly Gly Ala Glu Ala Arg Ile
        115                 120                 125

Asn Thr Gln Trp Leu Leu Thr Ser Gly Thr Thr Glu Ala Asn Ala Trp
    130                 135                 140

Lys Ser Thr Leu Val Gly His Asp Thr Phe Thr Lys Val Lys Pro Ser
145                 150                 155                 160

Ala Ala Ser Ile Asp Ala Ala Lys Lys Ala Gly Val Asn Asn Gly Asn
                165                 170                 175

Pro Leu Asp Ala Val Gln Gln
            180
```

-continued

<210> SEQ ID NO 2
<211> LENGTH: 127
<212> TYPE: PRT
<213> ORGANISM: Streptomyces avidinii

<400> SEQUENCE: 2

Ala Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 3
<211> LENGTH: 127
<212> TYPE: PRT
<213> ORGANISM: Artificial sequence
<220> FEATURE:
<223> OTHER INFORMATION: Synthetic peptide

<400> SEQUENCE: 3

Ala Glu Ala Gly Ile Thr Gly Thr Trp Tyr Ala Gln Leu Gly Asp Thr
1               5                   10                  15

Phe Ile Val Thr Ala Gly Ala Asp Gly Ala Leu Thr Gly Thr Tyr Glu
            20                  25                  30

Ala Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 4
<211> LENGTH: 133
<212> TYPE: PRT
<213> ORGANISM: Streptomyces avidinii
<220> FEATURE:
<221> NAME/KEY: MISC_FEATURE
<222> LOCATION: (128)..(133)
<223> OTHER INFORMATION: Poly-Histidine Tag

<400> SEQUENCE: 4

Ala Glu Ala Gly Ile Thr Gly Thr Trp Tyr Asn Gln Leu Gly Ser Thr
1               5                   10                  15

```
Phe Ile Val Thr Ala Gly Ala Asp Gly Ala Leu Thr Gly Thr Tyr Glu
             20                  25                  30

Ser Ala Val Gly Asn Ala Glu Ser Arg Tyr Val Leu Thr Gly Arg Tyr
         35                  40                  45

Asp Ser Ala Pro Ala Thr Asp Gly Ser Gly Thr Ala Leu Gly Trp Thr
     50                  55                  60

Val Ala Trp Lys Asn Asn Tyr Arg Asn Ala His Ser Ala Thr Thr Trp
 65                  70                  75                  80

Ser Gly Gln Tyr Val Gly Gly Ala Glu Ala Arg Ile Asn Thr Gln Trp
                 85                  90                  95

Leu Leu Thr Ser Gly Thr Thr Glu Ala Asn Ala Trp Lys Ser Thr Leu
             100                 105                 110

Val Gly His Asp Thr Phe Thr Lys Val Lys Pro Ser Ala Ala Ser His
         115                 120                 125

His His His His His
        130
```

<210> SEQ ID NO 5
<211> LENGTH: 127
<212> TYPE: PRT
<213> ORGANISM: Artificial sequence
<220> FEATURE:
<223> OTHER INFORMATION: Synthetic peptide

<400> SEQUENCE: 5

```
Ala Glu Ala Gly Ile Thr Gly Thr Trp Tyr Asn Gln Leu Gly Ser Thr
 1               5                  10                  15

Phe Ile Val Thr Ala Gly Ala Asp Gly Ala Leu Thr Gly Thr Tyr Glu
             20                  25                  30

Ser Ala Val Gly Asn Ala Glu Ser Arg Tyr Val Leu Thr Gly Arg Tyr
         35                  40                  45

Asp Ser Ala Pro Ala Thr Asp Gly Ser Gly Thr Ala Leu Gly Trp Thr
     50                  55                  60

Val Ala Trp Lys Asn Asn Tyr Arg Asn Ala His Ser Ala Ile Thr Trp
 65                  70                  75                  80

Ser Gly Gln Tyr Val Gly Gly Ala Glu Ala Arg Ile Asn Thr Gln Trp
                 85                  90                  95

Leu Leu Thr Ser Gly Thr Thr Glu Ala Asn Ala Trp Lys Ser Thr Leu
             100                 105                 110

Val Gly His Asp Thr Phe Thr Lys Val Lys Pro Ser Ala Ala Ser
         115                 120                 125
```

<210> SEQ ID NO 6
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 6
ggcacctggt acgcccagct gggagacacc ttcatcgtta c       41

<210> SEQ ID NO 7
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 7

```
gtaacgatga aggtgtctcc cagctgggcg taccaggtgc c                 41

<210> SEQ ID NO 8
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 8
tctgaccggt acctacgaag ccgctgttgg taacgctgaa t                 41

<210> SEQ ID NO 9
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 9
attcagcgtt accaacagcg gcttcgtagg taccggtcag a                 41

<210> SEQ ID NO 10
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 10
cgctcactcc gctatcacct ggtctggcc                               29

<210> SEQ ID NO 11
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 11
ggccagacca ggtgatagcg gagtgagcg                               29

<210> SEQ ID NO 12
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 12
tccagaattc gtaactaact aaaggaga                                28

<210> SEQ ID NO 13
<211> LENGTH: 52
<212> TYPE: DNA
<213> ORGANISM: Artificial sequence
<220> FEATURE:
<223> OTHER INFORMATION: Synthetic oligonucleotide

<400> SEQUENCE: 13
agacaagctt ttattaatgg tggtgatggt gatgggaagc agcggacggt tt     52

<210> SEQ ID NO 14
<211> LENGTH: 52
<212> TYPE: DNA
<213> ORGANISM: Artificial sequence
```

```
<220> FEATURE:
<223> OTHER INFORMATION: Synthetic oligonucleotide

<400> SEQUENCE: 14
ccggtcggcc tgaacgatat cttcgaggcc cagaagatcg agtggcacga ga            52

<210> SEQ ID NO 15
<211> LENGTH: 52
<212> TYPE: DNA
<213> ORGANISM: Artificial sequence
<220> FEATURE:
<223> OTHER INFORMATION: Synthetic oligonucleotide

<400> SEQUENCE: 15
gatctctcgt gccactcgat cttctgggcc tcgaagatat cgttcaggcc ga            52
```

MONOVALENT STREPTAVIDIN COMPOSITIONS

GOVERNMENT SUPPORT

This invention was made in part with government support under grant number P20GM072029-01 from the National Institutes of Health (NIH). The United States Government may have certain rights in this invention.

FIELD OF THE INVENTION

The invention relates, in part, to monovalent streptavidin compositions and methods of preparing and using monovalent streptavidin compositions. The compositions include monovalent streptavidin with a single femtomolar biotin-binding site.

BACKGROUND OF THE INVENTION

Streptavidin is used ubiquitously in biology because of the affinity and stability of its binding to biotin (Green, N. M., Methods in Enzymol. 184: 51-67, 1990). Streptavidin binds biotin with a femtomolar dissociation constant (Green, N. M. Methods in Enzymol. 184: 51-67, 1990). This tight and specific binding has led to the use of streptavidin for labeling and purification of biotinylated proteins, DNA and cells, for targeting of therapeutics proteins and drugs, for assembly of nanodevices. However, streptavidin is a tetramer, which permits binding to multiple binding sites and can result in cross-linking of the bound molecules. The occurrence of cross-linking makes streptavidin tetramers unsuitable for many applications. Mutations that make the streptavidin protein monomeric do reduce cross-linking, but also reduce the biotin binding affinity by $10^4$ to $10^5$-fold (Qureshi, M. H. et al., J Biol. Chem. 276: 46422-46428, 2001; Green, N. M. and Toms, J. C., Biochem. J. 133: 687-700, 1973; Laitinen, O. H. et al., J. Biol. Chem. 278: 4010-4014, 2003; Wu, S. C. and Wong, S. L., J. Biol. Chem. 280: 23225-23231, 2005), because part of the biotin binding site comes from a neighboring subunit (Chilkoti, A. et al., Proc. Natl. Acad. Sci. USA 92: 1754-1758, 1995; Sano, T and Cantor, C. R. Proc. Natl. Acad. Sci. USA 92: 3180-3184, 1995).

Efforts have been made to reduce the multiple binding issues of streptavidin tetramers. Single mutations in the biotin binding site have been identified that reduce biotin binding affinity dramatically (Qureshi, M. H. et al., J Biol. Chem. 276: 46422-46428, 2001; Chilkoti, A. et al., Proc. Natl. Acad. Sci. USA 92: 1754-1758, 1995; Klumb, L. A. et al., Biochem. 37: 7657-7663, 1998), but these mutations can still leave $K_d$ values in the nanomolar range and can disrupt tetramerization (Qureshi, M. H. et al., J Biol. Chem. 276: 46422-46428, 2001; Wu, S. C. and Wong, S. L., J. Biol. Chem. 280: 23225-23231, 2005). The double mutant N23A, S27D has one of the weakest reported affinities for biotin ($K_d 7.1 \times 10^{-5}$ M) (Chen, I. and Ting, A. Y. Curr. Opin. Biotechnol. 16: 35-40, 2005) and is still a tetramer, but each monomer subunit can still bind biotinylated cells and thus the potential for cross-linking remains.

SUMMARY OF THE INVENTION

The invention relates, in part, to compositions comprising a monovalent streptavidin tetramer, the production of the monovalent streptavidin tetramer, and its use in methods such as research, diagnostics, imaging, biomolecule labeling, single-particle tracking, nanotechnology, etc. The monovalent compositions of the invention are advantageous in that they tightly bind biotin and compounds comprising biotin but because only a single functional biotin binding site is present in each tetramer, cross-linking does not occur.

The invention also relates, in part, to compositions comprising streptavidin tetramers with 2 or 3 modified monomer subunits, with the remainder of the four subunits of the tetramer as wild-type streptavidin subunits. These chimeric streptavidin tetramers are useful when controlled multivalency is desired. The methods provided herein for producing such chimeric tetramers, and the multivalent tetramers of the invention may be useful for the construction of streptavidin-based conjugates with a defined number of binding sites for proteins fused to streptavidin-binding peptides (Keefe, A. D. et al., Protein Expr. Purif. 23: 440-446, 2001; Lamla, T. and Erdmann, V. A. Protein Expr. Purif. 33: 39-47, 2004; Schmidt, T. G. and Skerra, A. J. Chromatogr. A 676: 337-345, 1994), or for DNA and RNA aptamers (Bittker, J. A. et al., Nat. Biotechnol. 20: 1024-1029, 2002; Srisawat, C. and Engelke, D. R. RNA 7: 632-641, 2001).

According to one aspect of the invention, monovalent streptavidin tetramers are provided. The monovalent streptavidin tetramers include three modified streptavidin monomer subunits and one wild-type streptavidin monomer subunit, wherein the modified streptavidin monomer subunits each bind biotin or a fragment thereof with a $K_d$ of greater than or equal to about $5 \times 10^{31\ 4}$ M. In some embodiments, the wild-type streptavidin monomer subunit binds biotin or a fragment thereof, with a $K_d$ of a wild-type streptavidin monomer subunit for binding biotin or a fragment thereof. In some embodiments, the monovalent streptavidin tetramer has a proximal streptavidin $K_d$ for binding biotin or a fragment thereof. In certain embodiments, monovalent streptavidin tetramer has a single femtomolar biotin binding site. In some embodiments, the monovalent streptavidin tetramer has a proximal streptavidin overall biotin off-rate. In some embodiments, the amino acid sequence of the modified streptavidin monomer subunit has the amino acid sequence of a wild-type streptavidin monomer subunit with at least three substituted amino acid residues. In certain embodiments, the substituted amino acid residues are in the sequence of a biotin binding pocket of the streptavidin monomer subunit. In some embodiments, the three substituted amino acid residues are N23A, S27D, and S45A. In certain embodiments, one or more of the modified or wild-type streptavidin monomer subunits includes a purification tag. In some embodiments, the purification tag is a polyhistidine tag. In some embodiments, the streptavidin monomer subunit that includes the purification tag is the wild-type streptavidin monomer subunit. In certain embodiments, the monovalent streptavidin tetramer includes a detectable label. In some embodiments, the monovalent streptavidin tetramer is made by mixing together streptavidin monomers under conditions in which the monomers associate into tetramers.

According to another aspect of the invention, monovalent streptavidin tetramers are provided. The monovalent streptavidin tetramers include three modified streptavidin monomer subunits and one wild-type streptavidin monomer subunit, wherein the wild-type streptavidin monomer subunit binds biotin or a fragment thereof with a $K_d$ of a wild-type streptavidin monomer binding biotin or a fragment thereof. In some embodiments, the modified streptavidin monomer subunits bind biotin or fragment thereof with a $K_d$ of greater than or equal to about $5 \times 10^{-4}$ M. In certain embodiments, the monovalent streptavidin tetramer has a proximal streptavidin $K_d$ for binding biotin or a fragment thereof. In some embodiments, the monovalent streptavidin tetramer has a single femtomolar biotin binding site. In some embodiments, the monovalent streptavidin tetramer has a proximal streptavidin overall biotin off-rate. In some embodiments, the amino acid sequence of the modified streptavidin monomer subunit has the amino acid sequence of a wild-type streptavidin monomer subunit with at least three substituted amino acid residues. In certain embodiments, the substituted amino acid residues are in the sequence of a biotin binding pocket of the streptavidin monomer subunit. In some embodiments, the three substituted amino acid residues are N23A, S27D, and S45A. In some embodiments, one or more of the modified or wild-type streptavidin monomer subunits includes a purification tag. In certain embodiments, the purification tag is a polyhistidine tag. In some embodiments, the streptavidin monomer subunit that includes the purification tag is the wild-type streptavidin monomer subunit. In some embodiments, the monovalent streptavidin tetramer includes a detectable label. In certain embodiments, the monovalent streptavidin tetramer is made by mixing together streptavidin monomers under conditions in which the monomers associate into tetramers.

According to yet another aspect of the invention, monovalent streptavidin tetramers are provided. The monovalent streptavidin tetramers include three modified streptavidin monomer subunits and one wild-type streptavidin monomer subunit, wherein the monovalent streptavidin tetramer has a proximal streptavidin $K_d$ for binding biotin or a fragment thereof. In some embodiments, the wild-type streptavidin monomer subunit binds biotin or a fragment thereof, with a $K_d$ of a wild-type streptavidin monomer subunit for biding biotin or a fragment thereof. In some embodiments, the modified streptavidin monomer subunits each bind biotin or a fragment thereof with a $K_d$ of greater than or equal to about $5 \times 10^{-4}$ M. In some embodiments, the monovalent streptavidin tetramer has a single femtomolar biotin binding site. In certain embodiments, the monovalent streptavidin tetramer has a proximal streptavidin overall biotin off-rate. In some embodiments, the amino acid sequence of the modified streptavidin monomer subunit consists of the amino acid sequence of a wild-type streptavidin monomer subunit with at least three substituted amino acid residues. In certain embodiments, the substituted amino acid residues are in the sequence of a biotin binding pocket of the streptavidin monomer subunit. In certain embodiments, the three substituted amino acid residues are N23A, S27D, and S45A. In some embodiments, one or more of the modified or wild-type streptavidin monomer subunits includes a purification tag. In some embodiments, the purification tag is a polyhistidine tag. In some embodiments, the streptavidin monomer subunit that includes the purification tag is the wild-type streptavidin monomer subunit. In certain embodiments, the monovalent streptavidin tetramer includes a detectable label. In some embodiments, the monovalent streptavidin tetramer is made by mixing together streptavidin monomers under conditions in which the monomers associate into tetramers.

According to another aspect of the invention, streptavidin monomer subunits are provided. The streptavidin monomer subunits include a modified wild-type streptavidin monomer amino acid sequence and bind biotin or a fragment thereof with a $K_d$ of greater than or equal to about $5 \times 10^{-4}$ M. In some embodiments, the amino acid sequence of the modified streptavidin monomer subunit consists of the amino acid sequence of a wild-type streptavidin monomer subunit with at least three substituted amino acid residues. In certain embodiments, the substituted amino acid residues are in the sequence of a biotin binding pocket of the streptavidin monomer subunit. In some embodiments, the three substituted amino acid residues are N23A, S27D, and S45A. In some embodiments, the streptavidin monomer subunit is associated with three additional streptavidin monomer subunits in the form of a streptavidin tetramer. In certain embodiments, the streptavidin monomer subunits of the streptavidin tetramer that are not a streptavidin monomer subunit, are unmodified wild-type streptavidin monomer subunits. In some embodiments, the streptavidin monomer subunit includes a purification tag. In some embodiments, the streptavidin monomer subunit includes a detectable label.

According to yet another aspect of the invention, methods of making a plurality of monovalent streptavidin tetramers are provided, wherein the tetramers are formed by associating wild-type streptavidin monomer subunits and modified streptavidin monomer subunits, wherein the monovalent streptavidin tetramer has one or more of the following characteristics: (a) a proximal streptavidin $K_d$ for binding biotin or a fragment thereof, (b) a single femtomolar biotin binding site, (c) a proximal streptavidin overall biotin off-rate, and wherein a streptavidin monomer subunit modification has at least the substituted amino acid residues N23A, S27D, and S45A in the amino acid sequence of the streptavidin monomer subunit and the unmodified streptavidin monomer subunit is a wild-type streptavidin monomer subunit. In certain embodiments, the monovalent streptavidin tetramer includes a purification tag permitting monitoring of streptavidin monomer subunit association into tetramers having specific stoichiometric ratios of modified and unmodified streptavidin monomer subunits. In some embodiments, the purification tag is a polyhistidine tag. In certain embodiments, the purification tag is attached to the unmodified streptavidin monomer subunit. In some embodiments, the monovalent streptavidin tetramers include a detectable label. In some embodiments, the wild-type and modified monomers are associated by mixing monomers under conditions under which the monomers associate into tetramers.

According to yet another aspect of the invention, a composition is provided that includes monovalent streptavidin tetramers made by the any embodiment of the foregoing aspect of the invention.

According to yet another aspect of the invention, streptavidin tetramers are provided. The streptavidin tetramers include N=1, 2, or 3 modified streptavidin monomer subunits and 4 minus N wild-type streptavidin monomer subunits, wherein: (a) each wild-type streptavidin monomer subunit binds biotin or a fragment thereof with a $K_d$ of a wild-type streptavidin monomer subunit for binding biotin or a fragment thereof, (b) each modified streptavidin monomer subunit binds biotin or a fragment thereof with a $K_d$ of greater than or equal to about $5 \times 10^{-4}$ M, and (c) the streptavidin tetramer has a proximal streptavidin $K_d$ for binding biotin or a fragment thereof. In certain embodiments, the streptavidin tetramer has 4 minus N femtomolar biotin binding sites. In some embodiments, the tetramer has a proximal streptavidin overall biotin off-rate. In some embodiments, the sequence of the modified streptavidin monomer subunit consists of the sequence of a wild-type streptavidin monomer subunit with at least three substituted amino acid residues. In certain embodiments, the substituted amino acid residues are in the sequence of a biotin binding pocket of the streptavidin monomer subunit. In some embodiments, three of the three or more substituted amino acid residues are N23A, S27D, and S45A. In some embodiments, one or more of the streptavidin monomer subunits include a purification tag. In certain embodiments, the purification tag is a polyhistidine tag. In some embodiments, the streptavidin monomer subunit that includes the purification tag is the wild-type streptavidin monomer subunit. In some embodiments, one or more of the streptavidin monomer subunits includes a detectable label. In some embodiments, the ratio of modified and unmodified streptavidin monomer subunits in the streptavidin tetramer is 3:1, 2:2, or 1:3. In certain embodiments, the streptavidin tetramers are made by mixing wild-type and modified monomers under conditions under which the monomers associate into tetramers.

According to yet another aspect of the invention, a plurality of streptavidin tetramers is provided, wherein the tetramers streptavidin tetramers of the aforementioned aspect of the invention and the plurality includes streptavidin tetramers that have a ratio of wild-type streptavidin monomer subunits to modified monomer subunits of 1:3, 2:2, or 3:1, or a mixture thereof.

According to yet another aspect of the invention, methods of making a plurality streptavidin tetramer that includes 1, 2, or 3 modified streptavidin monomer subunits are provided. The methods include forming the tetramer by associating wild-type streptavidin monomers with modified streptavidin monomers, wherein the streptavidin tetramers have one or more of the following characteristics: (a) each wild-type streptavidin monomer subunit binds biotin or a fragment thereof a with a $K_d$ of a wild-type streptavidin monomer subunit for binding biotin or a fragment thereof, (b) the modified streptavidin monomer subunits bind biotin or a fragment thereof with a $K_d$ of greater than or equal to about $5 \times 10^{-4}$ M, and (c) the streptavidin tetramer has a proximal streptavidin $K_d$ for binding biotin or a fragment thereof, and (d) the tetramer has a proximal streptavidin $K_d$ for binding biotin or a fragment thereof. In some embodiments, each wild-type streptavidin monomer subunit comprises a femtomolar biotin binding site. In certain embodiments, the tetramer has a proximal overall biotin off-rate. In some embodiments, the amino acid sequence of the modified streptavidin monomer subunit consists of the amino acid sequence of a wild-type streptavidin monomer subunit with at least three substituted amino acid residues. In some embodiments, the substituted amino acid residues are in the sequence of a biotin binding pocket of the streptavidin monomer. In certain embodiments, three of the three or more substituted amino acid residues are N23A, S27D, and S45A. In some embodiments, one or more of the modified and/or wild-type streptavidin monomer subunits includes a purification tag. In certain embodiments, the purification tag is a polyhistidine tag. In some embodiments, the streptavidin monomer subunit that includes the purification tag is the wild-type streptavidin monomer subunit. In some embodiments, one or more of the streptavidin monomer subunits includes a detectable label. In some embodiments, the ratio of modified and unmodified streptavidin monomer subunits in the streptavidin tetramers is 3:1, 2:2, 1:3 or a mixture thereof. In certain embodiments, the wild-type and modified monomers are associated by mixing monomers under conditions under which the monomers associate into tetramers.

According to yet another aspect of the invention, a composition is provided that includes streptavidin tetramers made by the any embodiment of the aforementioned aspects of the invention.

According to another aspect of the invention, methods of binding biotin or a fragment are provided. The methods include contacting a biological sample that includes biotin or a fragment thereof with a monovalent streptavidin tetramer of an embodiment of any of the aforementioned monovalent streptavidin tetramers or made by an embodiment of any of the aforementioned methods under conditions that permit binding of biotin or a fragment thereof with a monovalent streptavidin tetramer.

According to another aspect of the invention, methods of binding biotin or a fragment thereof are provided. The methods include contacting a biological sample that includes biotin or a fragment thereof with a streptavidin tetramer of an embodiment of any of the aforementioned streptavidin tetramers or made by an embodiment of any of the aforementioned methods under conditions that permit binding of biotin or a fragment thereof with a streptavidin tetramer.

In some aspects, the invention includes the use of the foregoing tetramers and compositions in the preparation of a medicament.

These and other objects of the invention will be described in further detail in connection with the detailed description of the invention.

BRIEF DESCRIPTION OF THE DRAWINGS

FIG. 1 shows schematic diagrams and digitized images of SDS-PAGE gels summarizing the generation of monovalent streptavidin.

FIG. 2 shows digitized images of SDS-PAGE gels illustrating the stability of monovalent streptavidin.

FIG. 4 shows two graphs indicating the comparative $K_d$ of the dead tetramer D4 and monovalent streptavidin A1D3.

FIG. 5 shows three graphs illustrating the monovalent streptavidin off-rate.

BRIEF DESCRIPTION OF THE SEQUENCES

Figure 1A:
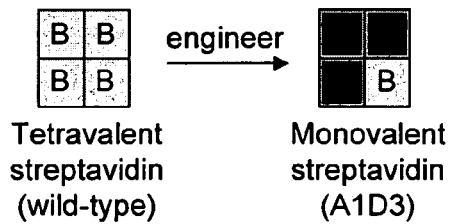
FIG. 1A is a schematic diagram of monovalent streptavidin structure. Wild-type streptavidin is a tetramer with 4 biotin binding sites (B=biotin). Monovalent streptavidin is a tetramer with 3 inactive subunits (dark grey squares) and one subunit that binds biotin with wild-type affinity (light grey square).

SEQ ID NO:1 is wild-type streptavidin sequence from Genbank Accession No. P22629:

MRKIVVAAIAVSLTTVSITASASADPSKDSKAQVSAAEAGITGTWYNQLG

STFIVTAGADGALTGTYESAVGNAESRYVLTGRYDSAPATDGSGTALGWT

VAWKNNYRNAHSATTWSGQYVGGAEARINTQWLLTSGTTEANAWKSTLVG

HDTFTKVKPSAASIDAAKKAGVNNGNPLDAVQQ

SEQ ID NO:2 is wild-type core streptavidin protein:

AEAGITGTWYNQLGSTFIVTAGADGALTGTYESAVGNAESRYVLTGRYDS

APATDGSGTALGWTVAWKNNYRNAHSATTWSGQYVGGAEARINTQWLLTS

GTTEANTLVGHDTFTKVKPSAAS

SEQ ID NO:3 is modified streptavidin monomer Dead (D), N23A, S27D, S45A:

AEAGITGTWYAQLGDTFIVTAGADGALTGTYEAAVGNAESRYVLTGRYDS

APATDGSGTALGWTVAWKNNYRNAHSATTWSGQYVGGAEARINTQWLLTS

GTTEANAWKSTLVGHDTFTKVKPSAAS

SEQ ID NO:4 is unmodified streptavidin monomer Alive (A) with polyhistidine tag:

AEAGITGTWYNQLGSTFIVTAGADGALTGTYESAVGNAESRYVLTGRYDS

APATDGSGTALGWTVAWKNNYRNAHSATTWSGQYVGGAEARINTQWLLTS

GTTEANAWKSTLVGHDTFTKVKPSAASHHHHHH

SEQ ID NO:5 is modified streptavidin monomer, T90I:

AEAGITGTWYNQLGSTFIVTAGADGALTGTYESAVGNAESRYVLTGRYDS

APATDGSGTALGWTVAWKNNYRNAHSAITWSGQYVGGAEARINTQWLLTS

GTTEANAWKSTLVGHDTFTKVKPSAAS

SEQ ID NO:6 is sequence to introduce N23A and S27D:

5'-ggcacctggtacgcccagctgggagacaccttcatcgttac-3'.

SEQ ID NO:7 is reverse complement of SEQ ID NO:6

5'-gtaacgatgaaggtgtctcccagctgggcgtaccaggtgcc-3'.

SEQ IN NO:8 is sequence to introduce S45A:

5'-tctgaccggtacctacgaagccgctgttggtaacgctgaat-3'.

SEQ ID NO:9 is reverse complement of SEQ ID NO:8:

5'-attcagcgttaccaacagcggcttcgtaggtaccggtcaga-3'.

SEQ ID NO:10 is primer sequence to introduce T90I:

5'-cgctcactccgctatcacctggtctggcc-3'.

SEQ ID NO:11 is reverse complement of SEQ ID NO:10:

5'-ggccagaccaggtgatagcggagtgagcg-3'.

SEQ ID NO:12 is forward primer sequence to add six histidine residues at the C-terminus of streptavidin sequence 5'-tccagaattcgtaactaactaaaggaga-3'.

SEQ ID NO:13 is reverse primer sequence to add six histidine residues at the C-terminus of streptavidin: 5'-agacaagcttttaftaatggtggtgatggtgatgggaagcagcggacggttt-3'.

SEQ ID NO: 14:
5'-ccggtcggcctgaacgatatcttcgaggcccagaagatcgagtggcacgaga-3'.

SEQ ID NO: 15:
5'-gatctctcgtgccactcgatcttctgggcctcgaagatatcgttcaggccga-3'.

Detailed Description Of The Invention

Novel monovalent streptavidin tetramers have been developed that have a single femtomolar biotin-binding site that retains the binding affinity of a wild-type streptavidin tetramer. Monovalent streptavidin tetramers have been generated that containing three subunits that do not functionally bind biotin and one subunit with a wild-type biotin-binding pocket. The monovalent streptavidin tetramer that has been developed has similar affinity for biotin, off-rate, and thermostability to a wild-type streptavidin tetramer but is monovalent. Thus, monovalent streptavidin tetramers with only one functional biotin binding monomer subunit have been produced.

A monovalent streptavidin has been made that bound to biotin with an affinity and stability similar to wild-type streptavidin, but did not produce cross-linking. Monovalent streptavidin should enable one to make use of femtomolar binding affinity without additional unwanted multimerization. Other chimeric streptavidin tetramers A2D2 and A3D1, have also been purified for when controlled multivalency is desired. This approach may be useful for the construction of streptavidin-based conjugates with a defined number of binding sites for proteins fused to streptavidin-binding peptides (Keefe, A. D. et al., Protein Expr. Purif. 23: 440-446, 2001; Lamla, T. and Erdmann, V. A. Protein Expr. Purif. 33: 39-47, 2004; Schmidt, T. G. and Skerra, A. J. Chromatogr. A 676: 337-345, 1994), or for DNA and RNA aptamers (Bittker, J. A. et al., Nat. Biotechnol. 20: 1024-1029, 2002; Srisawat, C. and Engelke, D. R. RNA 7: 632-641, 2001). Given the remarkable range of uses to which streptavidin has been put, these streptavidins should be valuable building blocks for many new nano-architectures.

The invention disclosed herein describes novel monovalent streptavidin tetramers and methods of making and using monovalent streptavidin tetramers and methods of making and using modified streptavidin monomers. The discovery that a monovalent streptavidin can be prepared that has a femtomolar binding affinity for biotin and fragments thereof, facilitates the production and use of such a monovalent streptavidin in research applications; clinical applications including, but not limited to, diagnostics; imaging methods; pharmaceutical delivery, e.g. delivery of drugs, toxins; as well as other art-known methods that include the use of streptavidin tetramers. The invention relates to the production and use of various streptavidin monomers and streptavidin tetramers.

The binding capacity of a streptavidin tetramer for biotin or a fragment thereof is referred to as its "valency". A monovalent streptavidin tetramer is a streptavidin tetramer that binds only a single biotin or fragment thereof. A multivalent streptavidin tetramer has the capacity to bind to two, three, or four biotin molecules or fragments thereof. Thus, a wild-type streptavidin tetramer would be a polyvalent streptavidin tetramer and could also be referred to as a tetravalent streptavidin tetramer because it can bind four biotin molecules or fragments thereof.

The invention relates, in part, to the preparation of streptavidin tetramers and the use of such streptavidin tetramers to bind biotin and biotin conjugates. The invention includes methods to associate the streptavidin monomer subunits with each other to prepare a streptavidin tetramer. In one method, streptavidin monomer subunits are prepared and the monomer subunits are associated by mixing streptavidin monomer subunits together under conditions that permit four monomers to associate to form a streptavidin tetramer. In streptavidin molecules so prepared, the streptavidin monomer subunits are non-covalently linked together. The terms "monomer", "subunit", and "monomer subunit" are used interchangeably herein.

A wild-type streptavidin tetramer includes four streptavidin wild-type monomers. A wild-type streptavidin monomer includes a single biotin binding site, also referred to herein as the biotin binding pocket, and is able to bind a single biotin molecule or fragment thereof. Thus, a wild-type streptavidin tetramer includes four biotin binding sites and is able to bind to four biotin molecules or fragments thereof. Streptavidin tetramers of the invention may include a combination of wild-type and modified streptavidin monomer subunits with the total number of subunits equal to four. Thus, streptavidin tetramers of the invention include tetramers with one, two, or three modified streptavidin monomers with the remaining monomers being wild-type monomers.

The streptavidin monomers and/or tetramers of the invention may be isolated monomers or tetramers. As used herein with respect to the monomers and tetramers provided herein, "isolated" means separated from its native environment and present in sufficient quantity to permit its identification or use. Isolated, when referring to a protein or polypeptide, means, for example: (i) selectively produced by monomer association methods or (ii) purified as by chromatography or electrophoresis. Isolated monomers or tetramers of the invention may be, but need not be, substantially pure. Because an isolated monomer or tetramer may be admixed with a pharmaceutically acceptable carrier in a pharmaceutical preparation, the polypeptide may comprise only a small percentage by weight of the preparation. The polypeptide is nonetheless isolated in that it has been separated from the substances with which it may be associated in production or living systems, i.e., isolated from other proteins, isolated from other types of monomers in the case of isolated monomers and isolated from other types of streptavidin tetramers in the case of isolated streptavidin tetramers. For example, a substantially pure streptavidin tetramer may be a tetramer that has a ratio of wild-type streptavidin monomers to modified streptavidin monomers of 1:3 that it is essentially free of streptavidin tetramers that have a ratio of wild-type streptavidin monomers to modified streptavidin monomers of 2:2 or 3:1. Substantially pure streptavidin tetramers may be produced by using the methods provided herein or using other art-known techniques.

A plurality of streptavidin tetramers of the invention may include streptavidin tetramers with a single ratio of wild-type streptavidin monomers to modified streptavidin monomers (e.g. 1:3, 2:2, or 3:1) or may be a mixture of tetramers that include two or more different ratios of wild-type streptavidin monomers to modified streptavidin monomers.

Pluralities of streptavidin molecules of the invention, in some embodiments, include only monovalent streptavidin tetramers. In other embodiments, a plurality of streptavidin tetramers of the invention may include bivalent, trivalent, or tetravalent tetramers. In some embodiments of the invention a plurality of streptavidin molecules may include mixtures of streptavidin molecules with different valences.

The streptavidin tetramers of the invention may be used in methods that include binding to biotin analogs. Examples of biotin analogs, although not intended to be limiting include: desthiobiotin, also known as dethiobiotin, selenobiotin, oxybiotin, homobiotin, norbiotin, iminobiotin, diaminobiotin, biotin sulfoxide, biotin sulfone, epibiotin, 5-hydroxybiotin, 2-thiobiotin, azabiotin, carbobiotin, and methylated derivatives of biotin, etc.

A wild-type streptavidin tetramer includes four wild-type monomer subunits, each of which binds biotin or a fragment thereof, with high affinity. The amino acid sequence of a wild-type streptavidin monomer subunit can be made from a precursor wild-type streptavidin protein that includes a core streptavidin sequence as well as a signal sequence. The complete sequence of wild-type streptavidin precursor protein is set forth as Genbank Accession No. P22629 and is referred to herein as SEQ ID NO:1. The skilled artisan will realize that conservative amino acid substitutions may be made in a wild-type streptavidin amino acid precursor or core sequence. As used herein, a "conservative amino acid substitution" refers to an amino acid substitution that does not alter the relative binding characteristics of the streptavidin monomer or tetramer for biotin or a fragment thereof, in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. A conservatively substituted wild-type streptavidin amino acid sequence will still be considered to be a wild-type strepavidin amino acid sequence as long as the streptavidin monomer (or tetramer made up of such monomers) retains the wild-type ability and affinity to bind biotin or a fragment thereof. Thus, a streptavidin monomer, or tetramer made with a wild-type streptavidin amino acid sequence that includes one or more conservative amino acid substitutions, will retain the functional capabilities of a wild-type streptavidin monomer or tetramer and be referred to as a wild-type streptavidin monomer or tetramer. Examples of conservative substitutions, although not intended to be limiting include E116A and T106A. (see Avantinis, S. K. et al., Chembiochem. 3(12): 1229-1234, 2002). Those of ordinary skill in the art will recognize additional conservative substitutions that do not negate the functional capability of wild-type streptavidin monomer or tetramer.

With respect to the identification of specific amino acid residues in polypeptides and proteins of the invention, residues 1-24 of the precursor protein sequence are removed by bacterial proteases, to yield the mature wild-type streptavidin protein. Residue 25 of the sequence set forth as Genbank Accession No. P22629 (SEQ ID NO:1) is considered to be residue one of the mature streptavidin. Residues 37-163 of the sequence set forth as SEQ ID NO:1 (with or without conservative amino acid substitutions) are considered to be the wild-type core streptavidin amino acid sequence. A wild-type core streptavidin amino acid sequence is set forth as SEQ ID NO:2. SEQ ID NO:4 also has a wild-type core streptavidin amino acid sequence and also has a polyhistidine purification tag attached. SEQ ID NO:3 is the sequence of a modified streptavidin monomer subunit. Core streptavidin includes the sequence of streptavidin with terminal amino acids removed, thereby improving biotin conjugate binding and protein stability (see Sano, T. et al., J Biol Chem. 270(47): 28204-28209, 1995). The streptavidin tetramers of the invention may also be made using recombinant core streptavidin sequences.

As used herein, a the term "wild-type streptavidin subunit" means a streptavidin subunit that has a wild-type streptavidin monomer amino acid sequence. As used herein, the term "unmodified" when used with respect to a streptavidin subunit means that monomer subunit has the core amino acid sequence of a wild-type streptavidin monomer subunit. Thus, in an unmodified streptavidin monomer subunit, the core amino acid sequence is the same as the core wild-type streptavidin monomer amino acid sequence. An example of an unmodified wild-type streptavidin subunit is an Alive (A) type monomer subunit provided herein.

SEQ ID NO:2 has the core wild-type streptavidin monomer amino acid sequence. SEQ ID NO:4 also has the core wild-type streptavidin monomer subunit amino acid sequence and a polyhistidine tag sequence. Additions of residues or other compounds onto the core sequence, such as those for a tag or label, do not negate the unmodified status of a streptavidin monomer as long as the core wild-type streptavidin monomer amino acid sequence remains unchanged. Thus, SEQ ID NO:2 and SEQ ID NO:4 (with a polyhistidine tag attached) are both examples of unmodified streptavidin monomer sequences. Tagging and/or labeling sequences or compounds can be added to a core wild-type streptavidin monomer amino acid sequence and the monomer remains an unmodified streptavidin monomer as long as the core amino acid sequence of the streptavidin monomer subunit remains unchanged from that of the core wild-type streptavidin monomer sequence.

A modified streptavidin monomer has a modification of the core wild-type streptavidin amino acid sequence. A modification of a sequence of a streptavidin subunit is a change in the amino acid sequence of the streptavidin monomer subunit from the wild-type amino acid sequence. Modifications of a streptavidin amino acid sequence may include the substitution of one or more amino acid residues in the sequence for alternative amino acids. A substitution of one amino acid for another in the mature sequence of wild-type streptavidin (residues 25-163 of SEQ ID NO:1), is an example of a modification of a streptavidin subunit. As described above herein, residue 25 of the sequence set forth as Genbank Accession No. P22629 (SEQ ID NO:1) is considered to be residue one of mature wild-type streptavidin monomer and residue 37 of SEQ ID NO:1 is considered to be residue one of the wild-type core streptavidin sequence. Using this numbering system the residues that are altered in the preparation of some modified monomers of the invention include residues N23, S27, and S45. An example of a modified streptavidin monomer subunit is a D subunit, which includes the following substitutions: N→A at position 23 in the amino acid sequence of mature wild-type streptavidin monomer; S→D at position 27 in the amino acid sequence of mature wild-type streptavidin monomer; and S→A at position 45 in the amino acid sequence of mature wild-type streptavidin monomer.

The sequence set forth as the Dead (D) monomer sequence includes the following substituted amino acid residues: N23A, S27D, and S45A (with the numbering based on the numbering of the mature wild-type streptavidin sequence, which corresponds to amino acids 25-163 of SEQ ID NO:1). A Dead monomer sequence of the invention is set forth herein as SEQ ID NO:3. The sequence of the Alive (A) monomer subunit, which as described above has the unmodified core wild-type streptavidin monomer sequence and may also include a $His_6$ purification tag. In some embodiments, an Alive (A) monomer does not have a purification tag. The Alive streptavidin monomer subunit with a $His_6$ tag is set forth herein as SEQ ID NO:4. For use in some methods and preparations of the invention, a sequence set forth as SEQ ID NO:2, 3, or 4 may be encoded in a plasmid with an initiating methionine, which is then removed by the E. coli. It will be understood that the presence of an initiating methionine is not an alteration of the core sequence thus is not a modification.

The invention includes in some aspects, a monovalent streptavidin tetramer. A monovalent streptavidin tetramer includes one wild-type streptavidin monomer subunit that maintains wild-type streptavidin binding affinity for biotin or fragments thereof, and three modified streptavidin subunits that have amino acid sequences that are modified from the wild-type streptavidin amino acid sequence. One type of modified streptavidin subunit used in a monovalent streptavidin tetramer of the invention is referred to herein as a Dead (D) type streptavidin monomer subunit and is a modified streptavidin monomer subunit. A preferred monovalent streptavidin tetramer of the invention includes wild-type monomer subunit and modified streptavidin subunits in a 1:3 ratio. A wild-type monomer subunit in the tetramer may be an Alive (A) type subunit. A monovalent streptavidin tetramer of the invention contains only a single functional biotin binding subunit. In some preferred monovalent streptavidin tetramers, all three modified streptavidin monomer subunits have the same type of sequence modification.

The wild-type streptavidin monomer subunit may, but need not, include a purification tag that may be used for the preparation and purification of monovalent streptavidin tetramers. An example of a methods for purification of a monovalent streptavidin tetramer that utilizes a purification tag is provided in the Examples section. An example of one alternative method of purifying a monovalent streptavidin tetramer without use of a purification tag includes separation of various tetramers with an iminobiotin column. With an iminobiotin column, D4 tetramers would not bind the column and other streptavidin tetramers would be eluted in the order A1D3, A2D2, A3D1, and then A4 with the later tetramers eluting with decreasing pH. Those of ordinary skill in the art will recognize that additional methods can also be used for separating and/or purifying streptavidin tetramers that have differing ratios of A to D streptavidin subunits.

Functional features of streptavidin tetramers and monomers can be determined and are useful for characterizing tetramers that include different combinations of wild-type and modified streptavidin monomer subunits. One such functional feature is a the binding affinity for biotin or a fragment thereof of a streptavidin monomer or tetramer. As is recognized in the art, binding affinity can be expressed in terms of the dissociation of bound biotin or a fragment thereof from the streptavidin monomer or tetramer to which it is bound. Thus, binding affinity can be expressed as the dissociation constant ($K_d$) of binding of a streptavidin monomer or tetramer for biotin or a fragment thereof. The binding affinity of a streptavidin monomer or tetramer can be determined as described below herein, or using other art-known methods. The binding affinity of a streptavidin monomer or tetramer of the invention can be compared to the binding affinity of a wild-type monomer or tetramer determined under substantially identical conditions. For example, if wild-type streptavidin tetramer is determined to have a $K_d$ of about $4.0 \times 10^{-14}$ M when binding biotin or a fragment thereof, a streptavidin tetramer of the invention can be tested under the same conditions to allow a comparison of the affinity of the streptavidin tetramer of the invention to that of a wild-type streptavidin tetramer.

In some instances, it may be desirable to have streptavidin monomers that have reduced level of biotin binding affinity (as compared to wild-type) and to use such a modified streptavidin monomer as a subunit of a streptavidin tetramer. Modified streptavidin monomers are provided herein that have a binding affinity significantly lower than wild-type streptavidin monomer biotin binding affinity. A Dead (D) streptavidin monomer subunit of the invention has much reduced or no functional binding to biotin or a fragment thereof. A Dead (D) streptavidin monomer subunit may have a $K_d$ of about 1 mM. In some embodiments, the $K_d$ of a Dead (D) subunit is greater than or equal to $5 \times 10^{-4}$ M. In certain embodiments, the $K_d$ of a Dead (D) subunit is greater than or equal to $5 \times 10^{-3}$ M (1 mM). In certain embodiments, the $K_d$ of a Dead (D) subunit is greater than or equal to $1 \times 10^{-3}$ M. In certain embodiments, the $K_d$ of a Dead (D) subunit is greater than or equal to $5 \times 10^{-4}$ M.

In some embodiments of the invention, the affinity of the Dead (D) subunit is so low as to result in essentially no functional binding of the Dead (D) monomer subunit to biotin or a fragment thereof. Thus, a streptavidin tetramer of the invention that includes three Dead (D) streptavidin monomer subunits and one wild-type streptavidin subunit will bind biotin or a fragment thereof at the single wild-type biotin binding site, and thus is defined as a monovalent streptavidin tetramer.

A monovalent streptavidin tetramer of the invention has a single biotin binding site and that has femtomolar binding affinity for biotin or a fragment thereof. As used herein, a femtomolar binding affinity means a $K_d$ of from about $1 \times 10^{-15}$ M to about $9.99 \times 10^{-13}$ M for that monomer binding site. The Alive (A) subunit in a monovalent streptavidin tetramer of the invention may bind biotin or a fragment thereof with a wild-type streptavidin monomer subunit binding affinity.

A monovalent streptavidin tetramer of the invention may have a proximal streptavidin $K_d$ for binding biotin or a fragment thereof. As used herein, the term "proximal streptavidin $K_d$" means having a $K_d$ that is between $1 \times 10^{-12}$ M and the $K_d$ of a wild-type streptavidin tetramer or up to 10-fold lower than the $K_d$ for wild-type streptavidin tetramers. Thus, a proximal streptavidin $K_d$ may be a level from $1 \times 10^{-12}$ down through the $K_d$ of wild-type streptavidin tetramer or below wild-type $K_d$ to as low as about $4 \times 10^{-15}$ M. Thus, a proximal streptavidin $K_d$ may be $1 \times 10^{-12}$ M, $5 \times 10^{-13}$ M, $1 \times 10^{-13}$ M, $5 \times 10^{-14}$ M or any level in between about $1 \times 10^{-12}$ M and about $4 \times 10^{-15}$ M.

A second functional feature of streptavidin tetramer and monomer binding that can be determined and may be useful to assess various tetramers and monomers of the invention is the off-rate of biotin from streptavidin after binding. Off-rate is a measure of time it takes for biotin to dissociate from a streptavidin monomer or tetramer to which it has bound. A faster off-rate indicates less stable binding than a streptavidin monomer or tetramer with a slower off-rate, which has more stable binding between the biotin and the streptavidin monomer or tetramer, respectively. A determination of the off-rate of biotin binding to a streptavidin monomer or tetramer thus can provide information regarding the stability of the binding. Off-rate determinations can be made using methods provided in the Examples section as well as using as additional art-known methods of measuring binding dissociation. A streptavidin monomer or tetramer of the invention may have a proximal overall biotin off-rate. As used herein, the term "proximal overall biotin off-rate" means that the percentage of biotin dissociation from the streptavidin monomer or tetramer is no more than 1%, 5%, 10%, 15%, 20%, or 25% higher (including all intervening percentages) than the percentage of biotin dissociation from a wild-type streptavidin monomer or tetramer, respectively, under substantially identical conditions. For example, the biotin off-rate of a streptavidin tetramer of the invention and a wild-type streptavidin tetramer can be determined under the essentially the same conditions and the percent dissociation of biotin from the streptavidin tetramer will be no more than 1%, 5%, 10%, 15%, 20%, or 25% higher (including all intervening percentages) than the percentage of biotin dissociation from a wild-type streptavidin tetramer.

There are also functional features of streptavidin tetramers that may be useful to assess various tetramers of the invention. One functional aspect that is useful to assess streptavidin tetramers is the stability of streptavidin tetramers over time. The stability of streptavidin tetramers involves a determination of whether a tetramer would rearrange its subunits over time. A rearrangement of subunits may include a change in the ratio of different types of monomers in a tetramer. For example, in a plurality of streptavidin tetramers that have a 3:1 ratio of a modified streptavidin monomers to wild-type streptavidin monomers, the ratio of subunit types may change over time, thus resulting in a mixed population of 3:1, 2:2, and 1:3 ratios of modified to wild-type streptavidin subunits. Low levels of stability result in faster shifts in streptavidin monomer ratios in a streptavidin tetramer and higher levels of stability result in reduced changes in the ratio of streptavidin subunit types in a streptavidin tetramer.

The thermostability of streptavidin tetramers is another functional feature that may be used to assess streptavidin tetramers of the invention. Thermal stability can be assessed by heating streptavidin tetramers as a determination of whether the streptavidin monomers remain associated in the tetramers or dissociate. In some embodiments, dissociation of monomeric subunits of tetramers means dissociation into monomeric subunits. In other embodiments, it may mean loss of one or more monomer subunits with dimer or trimer polymers remaining. Methods for determining thermostability of a streptavidin tetramers are provided herein and also include additional assessment methods known in the art.

The modified and wild-type monomers and the monovalent and polyvalent streptavidin tetramers of the invention may include a tag or label. In some embodiments, a tag is a purification tag. Purification tags of the invention include, but are not limited to polyhistidine tags (e.g. a $His_6$ tag). Additional types of purification tag sequences are known in the art and may be used in conjunction with the streptavidin tetramers of the invention. Examples of purification tags, although not intended to be limiting, include the HQ tag from Promega (Madison, Wis.) that has a sequence of HQHQHQ, a FLAG tag (DYKDDDDK), or numerous other epitope tags known in the art. See, for example, Jarvik, J. W. and Telmer, C. A., Annu. Rev. Genet. 32: 601-18, 1998.

In some embodiments of the invention, a streptavidin monomer subunit or streptavidin tetramer of the invention is linked to a detectable label. Detectable labels useful in the invention include, but are not limited to: a fluorescent label, an enzyme label, a radioactive label, visual label (e.g. a metallic label such as ferritin or gold), a nuclear magnetic resonance active label, an electron spin resonance label, a positron emission tomography label, a luminescent label, and a chromophore label. The detectable labels of the invention can be attached to the streptavidin monomer subunits or streptavidin tetramers of the invention by standard protocols known in the art. In some embodiments, the detectable labels may be covalently attached to a streptavidin monomer or tetramer of the invention. The covalent binding can be achieved either by direct condensation of existing side chains or by the incorporation of external bridging molecules. In some embodiments a detectable label may be attached to a streptavidin monomer or tetramer of the invention using genetic methods. In some embodiments, a label may be attached by conjugating a moiety of interest (e.g. the labeling moiety) to biotin or a biotin analog and then non-covalent binding to the streptavidin tetramer. In some embodiments of the invention, more than one type of detectable label may be attached to a streptavidin monomer or tetramer of the invention.

The streptavidin monomers and tetramers of the invention bind to biotin or fragments thereof. By biotin fragments is meant a fragment of biotin that is sufficiently unchanged from the structure of biotin to be recognized and bound by a streptavidin monomer or tetramer of the invention and or by a wild-type monomer or tetramer. The biotin fragments may be considered to be functional biotin fragments. By "functional" biotin fragments, is meant that the biotin fragment is recognized by and can be bound by a streptavidin monomer or tetramer of the invention.

The invention includes the use of a streptavidin monomer or tetramer of the invention to bind to a biotin molecule or fragment thereof that is conjugated to an additional molecule or compound. Examples of such molecules or compounds, though not intended to be limiting, include proteins, nucleic acids, fatty acids, carbohydrates, small molecules, enzymes, antibodies, drug molecules, chemical compounds, cells, etc. Biotin is extensively used by those of skill in the scientific arts in labeling and tracking methods. Therefore, one of ordinary skill in the art will recognize that the streptavidin molecules of the invention may be used to bind numerous different types of biotin conjugates. In some embodiments, a biotin or biotin molecule (conjugated or not) may be in solution or may be attached to a surface. Examples of surfaces to which a streptavidin tetramer of the invention may be attached include, but are not limited to, a magnetic or chromatographic bead or particle bead or a chromatography support or other support.

The streptavidin monomers and tetramers of the invention can be used for a wide variety of purposes including, but not limited to: cell sorting, cell labeling, drug delivery, imaging methods, etc. The streptavidin tetramers of the invention can be linked to labels, delivery molecules, cells, etc for use in various technologies. The streptavidin tetramers of the invention are also useful for imaging, including real-time imaging in vitro and in vivo.

An example of the use of a streptavidin tetramer of the invention, though not intended to be limiting, is the use of the streptavidin tetramer to isolate a target molecule or compound from a complex mixture or solution. In such embodiments, a streptavidin tetramer of the invention can be attached to a targeting molecule and contacted with the complex mixture. The targeting molecule, attached to the streptavidin tetramer, binds to the target and the complex mixture can be contacted with biotin or a fragment thereof, either alone, or in a conjugated form. Binding of the streptavidin tetramer of the invention to the biotin or fragment thereof enables detection of the bound target in the complex mixture. Additionally, standard separation methods can then be used to separate the bound target molecule or compound from the complex mixture using standard separation methods.

Another example of methods in which the streptavidin tetramers of the invention, including the monovalent streptavidin tetramers described herein, may be used is in single-particle tracking, which is described in the Examples section herein. Additional labeling, imaging, cell sorting, and delivery methods for which the streptavidin tetramers of the invention may be used, include a wide variety of art-known methods that include the use of streptavidin/biotin interactions.

Additional uses for streptavidin monomers and tetramers of the invention may also include control of assembly of nanodevices. For example, binding of controlled numbers of biotinylated DNA, biotinylated proteins or biotinylated inorganic particles (including carbon nanotubes and quantum dots) to a surface or bead for systems detecting biological analytes or for building electrical circuits. An example of an application is the targeting to chemically biotinylated erythrocytes of streptavidin bound to drugs or other proteins. Erythrocytes may be used as drug delivery vehicles and may be useful because of their long circulation time. Unlike this method of targeting with the streptavidin tetramers of the invention, previous targeting with biotin binding proteins has caused complement lysis of the erythrocytes from cross-linking of surface proteins (Muzykantov, V. R. et al., Anal Biochem 241(1): 109-119, 1996.

The invention will be more fully understood by reference to the following examples. These examples, however, are merely intended to illustrate the embodiments of the invention and are not to be construed to limit the scope of the invention.

EXAMPLES

Methods
General

Biotin (a gift from Tanabe USA; San Diego, Calif.) was dissolved in Dimethyl Sulfoxide (DMSO) at 100 mM. Sodium dodecyl sulfate-polyacrylamide gel electrophoresis (SDS-PAGE) was performed at 200 V with the gel box (X Cell SureLock, Invitrogen; Carlsbad, Calif.) surrounded by ice to prevent dissociation of the streptavidin subunits during electrophoresis.

Plasmid Construction

Wild-type core streptavidin in pET21a(+) (Novagen; San Diego, Calif.) was a kind gift from P. Stayton (University of Washington; Seattle, Wash.) (Klumb, L. A. et al., Biochemistry 37: 7657-7663, 1998). Mutations in streptavidin were generated by QuikChange™ (Stratagene; La Jolla, Calif.) using the following primers and their reverse complements: 5'-GGCACCTGGTACGCCCAGCTGGGAGA-CACCTTCATCGTTAC-3' (SEQ ID NO:6) to introduce N23A and S27D, 5'-TCTGACCGGTACCTACGAAGC-CGCTGTTGGTAACGCTGAAT-3' (SEQ ID NO:8) to introduce S45A, and 5' CGCTCACTCCGCTATCACCTG-GTCTGGCC-3' (SEQ ID NO:10) to introduce T90I. Mutations were confirmed by DNA sequencing. The reverse complements of SEQ ID NO:6, 8, and 10 are SEQ ID NO:7, 9, and 11, respectively. To generate the Alive streptavidin subunit (A), six histidine residues were added to the C-terminus by polymerase chain reaction (PCR) of streptavidin using the primers 5'-TCCAGAATTCGTAACTAACTAAAG-GAGA (SEQ ID NO:12) and 5'-AGACAAGCTTTTAT-TAATGGTGGTGATGGTGATGGGAAG-CAGCGGACGGTTT-3' (SEQ ID NO:13). This PCR product was cloned into the BamHI and HindIII sites of pET21a(+)-streptavidin (Klumb, L. A. et al. Biochemistry 37: 7657-7663, 1998). AP-neuroligin was generated from pEGFP-G1 containing mouse neuroligin-1 (Levinson, J. N. et al., J. Biol. Chem. 280: 17312-17319, 2005) by replacing Green Fluorescent Protein (GFP) with the acceptor peptide (AP) (Chen, I. et al., Nat. Methods 2: 99-104, 2005) at the AgeI and BglII sites, using the primers: 5'-CCGGTCGGCCTGAAC-GATATCTTCGAGGCCCAGAAGATC-GAGTGGCACGAGA-3' (SEQ ID NO:14) and 5'-GATCTCTCGTGCCACTCGATCT-TCTGGGCCTCGAAGATATCGTTCAGGCCGA-3', (SEQ ID NO:15) so that AP would be at the N-terminus of neuroligin-1. To make Ala-neuroligin, a lysine in the AP was mutated to alanine by QuikChange™ using the primers described in Chen et al. (Chen, I. et al., Nat. Methods 2: 99-104, 2005). The construction of AP-CFP-TM and Ala-CFP-TM plasmids has been described (Chen, I. et al., Nat. Methods 2: 99-104, 2005).

Streptavidin Expression and Purification

An overnight culture picked from a freshly grown colony of E. coli BL21 (DE3) was diluted 100-fold into LB ampicillin and grown to $OD_{600}$ 0.9 at 37° C. It was then induced with 0.5 mM isopropyl-beta-D-thiogalactopyranoside (IPTG) and incubated for a further 4 hr at 37° C. Inclusion bodies were purified using B-PER (Pierce; Rockford, Ill.), following manufacturer's instructions, and dissolved in 6 M guanidinium hydrochloride pH 1.5 (GuHCl). To generate chimeric streptavidins, the relative concentration of each unfolded subunit was estimated from $OD_{280}$ in GuHCl and subunits were mixed in the desired ratio. Subunits in GuHCl were refolded by rapid dilution into PBS, and concentrated by ammonium sulphate precipitation, following Schmidt et al. (Schmidt, T. G. & Skerra, A., J. Chromatogr. A 676: 337-345, 1994). The precipitate was re-dissolved in PBS and dialyzed three times against PBS. This step was sufficient to purify wild-type streptavidin, A4 and D4. To purify chimeric streptavidins, a Poly-Prep column (Bio-Rad; Hercules, Calif.) was loaded with 1.6 mL Ni-nitrilotriacetic acid agarose (Qiagen; Valencia, Calif.) and was washed with 8 mL of binding buffer (50 mM Tris base, 300 mM NaCl, pH 7.8), using gravity flow at room temperature. The streptavidin was diluted two-fold in binding buffer and loaded on the column. The column was washed with 8 mL washing buffer (binding buffer+10 mM imidazole) and then with 8 mL elution buffer 1 (binding buffer+70 mM imidazole, eluting principally A1D3). 0.5 mL fractions were collected from this elution and from subsequent elutions in 8 mL elution buffer 2 (binding buffer+100 mM imidazole, eluting principally A2D2) or 8 mL elution buffer 3 (binding buffer+125 mM imidazole, eluting principally A3D1). Fractions were mixed with 6× SDS-loading buffer (0.23 M Tris HCl pH 6.8, 24% v/v glycerol, 120 µM bromophenol blue, 0.4 M dithiothreitol, 0.23 M SDS) and were loaded without boiling onto 8% SDS-PAGE gels. Fractions of the correct composition, determined by comparison to the bands from the initial refold, were pooled and dialyzed in PBS. Streptavidin concentration was determined in PBS from $OD_{280}$ using $\epsilon_{280}$ of $34,000 M^{-1} \cdot cm^{-1}$ (Sano, T. and Cantor, C. R., Proc. Natl. Acad. Sci. U. S. A 87: 142-146, 1990). Where required, samples were concentrated using a Centricon Ultracel YM10 (Millipore; Billerica, Mass.).

Streptavidin tetramers are also purified by use of an iminobiotin column. Using this separation method various streptavidin tetramers with different ratios of D:A streptavidin subunits are separated from each other without the need to include a purification tag on the streptavidin tetramer. Dead (D4) tetramers, which have four D streptavidin subunits do not bind the column and other streptavidin tetramers are eluted in the order A1D3, A2D2, A3D1, and then A4 under decreasing pH conditions. Standard elution conditions are used. Iminobiotin is available from Pierce Biotechnology, Inc, Rockford, Ill.

Fluorophore Conjugation to Streptavidin

Streptavidin and its variants were labeled with Alexa Fluor 568 by adding 1/10 volume of 1 M $NaHCO_3$ pH 8.4 and then a 10-fold molar excess of Alexa Fluor 568 succinimidyl ester (Molecular Probes; Carlsbad, Calif.) (stock dissolved at 1 mg/mL in dry dimethylformamide) and incubating for 4 hr at room temperature. Free dye was separated on a NAP5 column (GE Healthcare; Amersham Biosciences, Piscataway, N.J.) following manufacturer's instructions. Fractions containing labeled protein, determined by running boiled samples on a 16% SDS-PAGE gel, were pooled and dye was further removed by two rounds of dialysis in PBS.

Mass Spectrometry

Biospin columns (Bio-Rad) were equilibrated by spinning 5 times in 500µL of 15 mM ammonium acetate pH 7.8 at 1000 g for 2 min. Then 30-50 µL of 30 µM protein in PBS was buffer-exchanged into 15 mM ammonium acetate pH 7.8 using the pre-equilibrated Biospin columns by spinning for 20 s at 1000 g. To ensure that PBS was completely removed, the flow-through was again buffer-exchanged with a second pre-equilibrated column for 20 s. This procedure also removed free biotin when the starting 30 µM streptavidin forms were incubated with 200 µM biotin. Less than 2 min before introducing into the mass spectrometer, the buffer-exchanged samples were diluted with a solution of 1:1 15 mM ammonium acetate pH 7.8 and 78% acetonitrile, 0.01% trifluoroacetic acid.

An Advion nanospray robot (Advion BioSystems, Ithica, N.Y.) with a back-pressure of 0.45 Psi introduced the samples into the mass spectrometer, an 8.5 Tesla custom-built Electrospray Ionisation-Fourier Transform Mass Spectrometer. To visualize the non-covalent tetramers and non-covalent biotin binding in the high m/z range, the following settings were used: Chirp rate=750 Hz, Amplitude=0.5 V p-p, Tube lens=200 V, Capillary heater 2 V, Quad filter=−20 V, Skimmer=0 V, Capillary offset=34 V, X-fer=−110 V, Leak gas=$4.2 \times 10^{-5}$ Torr. The capillary heater was kept low and the Quad filter and Skimmer were kept either high or off to prevent subunit dissociation. The transfer was set to this low value of −110 V in order to visualize the high m/z region.

The masses were calculated manually by first determining the charge state. The final mass was determined by multiplying the observed m/z by the charge and subtracting the mass corresponding to the addition of protons to give that charge. For example, for the 15+ charge state of D4 an m/z of 3534.159 was obtained. (15×3534.159)−(15×1.00727) gave a mass for this ion of 52,997 Da. This calculation was repeated for each charge state and the mean and standard deviation reported. The spectra were calibrated with tetrameric streptavidin, after its monomer mass was determined under denaturing conditions (Mr=13,271.4 Da). Average masses were predicted from the DNA sequence, using the ExPASy PeptideMass Calculator (ca.expasy.org/tools/peptide-mass.html) and assuming removal of the N-terminal formyl-Methionine.

$K_d$ Measurements

Figure 4A:
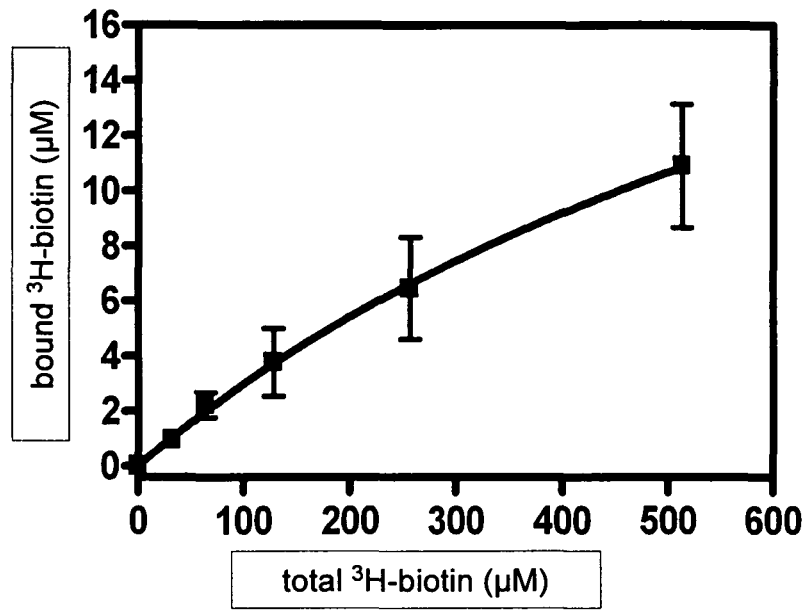
FIG. 4A shows the $K_d$ value determination for D4. 24 μM D4 was incubated with increasing concentrations of ³H-biotin. After >20 hr, the amount of bound ³H-biotin was determined by precipitating D4. Means of triplicate measurement are shown ±1 s.d. The measured $K_d$ for D4 was 9.18±1.17×10⁻⁴M (s.e.m.).

The $K_d$ of A1D3 streptavidin (A is "Alive" subunit; D is "Dead" subunit) was obtained using a competition assay modified from Klumb et al. (Klumb, L. A. et al., 1998. *Biochemistry* 37: 7657-7663). Wild-type streptavidin was depleted of the small amount of co-purifying monomeric streptavidin by gel filtration. Fully tetrameric wild-type streptavidin (60 nM each subunit) was mixed with 20 nM (Kada, G. et al., Biochim. Biophys. Acta 1427: 33-43, 1999; Bayer, E. A. et al., Electrophoresis 17: 1319-1324, 1996) $^3$H-biotin (Amersham; Piscataway, N.J.) and 0-1.4 μM of competing A1D3 in PBS pH 7.0. Mixtures were incubated at 37° C. for >20 hr to allow sufficient time for equilibration. To separate the His$_6$-tagged A1D3 from wild-type streptavidin, an equal volume of a 50% slurry of Ni-NTA beads (Qiagen) in PBS with 15 mM imidazole was added. After 1 hr at room temperature, the beads were cleared by centrifugation at 15,600 g for 1 min. Aliquots were taken from the supernatant containing the biotin-bound wild-type streptavidin, an equal volume of 10% SDS in water was added, and samples were heated to 95° C. for 30 min, and counted in a Beckman Coulter LS6500 Liquid Scintillation Counter. The $K_d$ ratio was obtained using Matlab (Mathworks; Natick, Mass.) using the formula from Klumb et al. (Klumb, L. A. et al. Biochemistry 37: 7657-7663, 1998). The affinity of A1D3 was calculated from this $K_d$ ratio multiplied by the previously determined $K_d$ of wild-type streptavidin for biotin of $4\times10^{-14}$M (Green, N. M. Methods Enzymol. 184: 51-67, 1990) and divided by four, since only one of the four subunits of A1D3 showed significant biotin binding (FIG. 4A).

It was difficult to detect biotin binding by D4 using a competition assay against wild-type streptavidin because of its extremely low binding affinity, and so the following assay was used instead to determine the $K_d$ (Reznik, G. O. et al., Proc. Natl. Acad. Sci. USA 95: 13525-13530, 1998): 24 μM D4 was incubated with 0-500 μM $^3$H-biotin in 100 μL total volume. After incubation at room temperature for 20 hr, the protein was precipitated by adding 50 μL to 200 μL 0.2 M ZnSO$_4$ followed by 200 μL 0.2 M NaOH. The protein precipitate was pelleted by centrifugation at 16,500 g for 5 min. The biotin bound by D4 was calculated from the total $^3$H-biotin added minus the $^3$H-biotin in the supernatant. The $K_d$ was obtained using a nonlinear regression analysis (one-site binding hyperbola) with SigmaPlot (Systat Software; Point Richmond, Calif.).

Off-Rate Assay

The off-rate of biotin-fluorescein from streptavidin was measured in PBS with 20 mM HEPES pH 7.4 (PBS-H) using a Safire plate-reader and XFluor4 software (Tecan US; Durham, N.C.) with 494 nm excitation and 527 nm emission. In this assay the binding of biotin-4-fluorescein to an excess of streptavidin results in quenching of fluorescein emission (Kada, G. et al. Biochim. Biophys. Acta 1427: 33-43, 1999). As the biotin-4-fluorescein dissociates, the fluorescence recovers. The assay was performed in the presence of excess biotin so that sites left open by biotin-4-fluorescein dissociation are immediately re-filled by biotin. Streptavidin tetramer at 1 μM in 10 μL PBS-H was added to 12 nM biotin-4-fluorescein (Molecular Probes) in 170 μL PBS-H and incubated for 30 min at 37° C. 20 μL PBS-H or 20 μL PBS-H 10 mM biotin was then added and recording immediately started, with incubation at 37° C. Percentage dissociation was calculated as (signal with biotin—signal without biotin)/(mean maximal signal of T90I with biotin—initial T90I signal without biotin)×100. The concentration of competing biotin was saturating, since reducing the biotin concentration ten-fold produced indistinguishable dissociation rates.

Thermostability Assay 2.3 μM wild-type streptavidin or chimeric streptavidin in PBS was heated at the indicated temperature for 3 min in a PTC-200 PCR machine (MJ Research; Waltham, Mass.) and then immediately placed on ice (Bayer, E. A. et al. Electrophoresis 17: 1319-1324, 1996). Samples were mixed with 6× SDS-PAGE loading buffer and loaded onto a 16% polyacrylamide gel.

Cell Culture, Biotinylation and Imaging

HeLa cells were grown in Dulbecco's Modified Eagle Medium (DMEM) with 10% Fetal Calf Serum, 50 U/mL penicillin and 50 μg/mL streptomycin. HeLa stably expressing AP-CFP-TM or Ala-CFP-TM have been previously described (Howarth, M. et al. Proc. Natl. Acad. Sci. USA 102: 7583-7588, 2005). Dissociated primary neuronal cultures were prepared from Embryonic Day 18 or 19 (E18/19) rats and transfected with Lipofectamine 2000 at DIV6 as in Levinson et al. (Levinson, J. N. et al. J. Biol. Chem. 280: 17312-17319, 2005).

Enzymatic biotinylation and imaging of HeLa transfectants were performed as previously described (Howarth, M. et al. Proc. Natl. Acad. Sci. USA 102: 7583-7588, 2005), except instead of 10 μM biotin and 1 mM ATP, we added 10 μM biotin-AMP (synthesized according to Coleman and Huang; Coleman, T. M. and Huang, F. Chem. Biol. 9: 1227-1236, 2002) to give equivalent biotinylation but minimizing the risk of purinoreceptor activation by ATP (Rathbone, M. P. et al., Prog. Neurobiol. 59: 663-690, 1999). HeLa transfectants were biotinylated for 10 min at room temperature, and stained with 10 μg/mL Alexa Fluor 568-conjugated wild-type streptavidin, D4 or A1D3 for 10 min at 4° C. Biotinylation of neurons was performed at day in vitro (DIV) 8 in Hanks' Balanced Salt Solution (HBSS) (Invitrogen) with 0.2 μM biotin ligase and 10 μM biotin-AMP for 5 min at 37° C. Neurons were then washed with HBSS and incubated for 2 min with 5 μg/mL Alexa Fluor 568-conjugated wild-type streptavidin (Molecular Probes) or A1D3 at 37° C. Neurons were washed with NeuroBasal media (Invitrogen) supplemented with B-27 (Invitrogen), 50 U/mL penicillin, 50 μg/mL streptomycin, and 0.2 mM L-glutamine and chased in the same medium for 0 or 2 hr at 37° C. Cells were then fixed in −20° C. methanol. There was no signal from wild-type streptavidin labeling if neurons were instead transfected with Ala-neuroligin-1 containing a point mutation in AP, confirming the specificity of labeling (Howarth, M. et al. Proc. Natl. Acad. Sci. USA 102: 7583-7588, 2005). To observe synapse formation, cells were biotinylated and stained with streptavidin as above, biotinylation and streptavidin staining was repeated at 6 hr, and then after 24 hr total chase cells were fixed in methanol. Samples were stained for pre-synaptic markers using guinea pig anti-VGLUT1 (1:1000, Chemicon; Temecula, Calif.), followed by goat anti-guinea pig Alexa Fluor 488 (1:1000, Molecular Probes). All antibody reactions were performed in blocking solution [PBS with 0.3% Triton X-100 and 2% normal goat serum (Vector Laboratories; Burlingame, Calif.)] for 1 hr at room temperature or overnight at 4° C.

Images of HeLa cells were collected on a Zeiss Axiovert 200M inverted epifluorescence microscope using a 40× oil-immersion lens and a MicroMAX CCD camera (Roper Scientific; Tucson, Ariz.). CFP (420DF20 excitation, 450DRLP dichroic, 475DF40 emission) and Alexa568 (560DF20 excitation, 585DRLP dichroic, 605DF30 emission) images were collected and analyzed using OpenLab software (Improvision; Lexington, Mass.). Fluorescence images were background-corrected. Neuron images were acquired on a Zeiss Axiovert 200M microscope with a 63× 1.4 NA Acromat oil-immersion lens and a monochrome 14-bit Zeiss Axiocam HR charged-coupled camera with 1300×1030 pixels. To correct for out-of-focus clusters within the field of view, focal plane z-stacks were acquired and maximum intensity projections performed off-line. Images were scaled to 16 bits and analyzed in Northern Eclipse (Empix Imaging; Ontario, Canada) with user-written software. Briefly, images were processed at a constant threshold level (of 32,000 pixel values) to create a binary mask image, which was multiplied with the original image using Boolean image arithmetic. The resulting image contained a discrete number of clusters with pixel values of the original image. Only dendritic clusters greater than 5 pixels in size, and with an average pixel values 2 times greater than background pixel values were used for analysis. Results were then calculated in terms of clusters per micrometer of dendrite. For assessment of pre-synaptic terminals, clusters were determined as before and average grey levels of clusters were compared between transfected dendrites and untransfected dendrites within the same field of view. The two-tailed parametric Student's t-test was performed to calculate statistical significance of results between experimental groups. "n" represents the number of transfected neurons for which clusters were measured.

7657-7663, 1998) but still leave $K_d$ values in the nanomolar range and disrupt tetramerization (Qureshi, M. H. et al., J Biol. Chem. 276: 46422-46428, 2001; Wu, S. C. and Wong, S. L., J. Biol. Chem. 280: 23225-23231, 2005). The double mutant N23A, S27D has one of the weakest reported affinities for biotin ($K_d$ 7.1×10$^{-5}$ M$^{10}$) and is still a tetramer. Nevertheless we observed that N23A, S27D streptavidin still bound to biotinylated cells. A triple mutant N23A, S27D, S45A was produced. The triple mutant N23A, S27D, S45A showed negligible biotin binding and left the tetramer structure intact. The binding of this triple mutant (composed of "Dead" sub-units-D in FIG. 1) was so weak that it was difficult to measure but a $K_d$ of 9.18±1.17×10$^{-4}$ M (s.e.m.) was obtained. (FIG. 4A). To generate monovalent streptavidin (FIG. 1B), the wild-type subunit was first tagged with a His$_6$-tag ("Alive" subunit-A in FIG. 1). Then D and A subunits were combined at a molar ratio of 3:1 in guanidinium hydrochloride and refolded by rapidly diluting the mixture into PBS. This refold generated a mix of tetramers of different compositions.

The different tetramers were purified using a Ni-nitrilotriacetic acid (NTA) column, eluting according to the number of His$_6$-tags with increasing concentrations of imidazole. The tetramers could be distinguished by SDS-PAGE, if the samples were not boiled, according to the number of His-tags present, showing that at least 30% were of the monovalent A1D3 form (FIG. 1C, lanes 1 and 3). Thus purified fractions of the monovalent A1D3 were obtained (final yield 2 mg/L), as well as the other chimeric streptavidins, A2D2 and A3D1. The tetramer composition was further confirmed by boiling the samples before loading on SDS-PAGE, to determine the ratio of A to D subunits (FIG. 1D), and by electrospray ionization mass spectrometry. In Table 1 (Schwartz, B. L. et al., J. of the Amer. Soc. for Mass Spec. 6: 459-465, 1995) the observed mass (±s.d.), determined by Electrospray Ionization-Mass Spectrometry, is compared to the mass predicted from the sequence. From the change (±s.e.m.) upon addition of biotin (mass 244.31), we determined how many biotin molecules were bound to each tetramer.

TABLE 1

Mass of different streptavidin tetramers with or without biotin.

| Tetramer | Predicted | Observed − biotin | Observed + biotin | Change + biotin | # biotins |
|---|---|---|---|---|---|
| D4 | 52,962 | 52,997 ± 4 | 52,996 ± 12 | −1 ± 2 | 0 |
| A1D3 | 53,816 | 53,848 ± 5 | 54,088 ± 6 | 240 ± 4 | 1 |
| A2D2 | 54,669 | 54,704 ± 6 | 55,193 ± 3 | 489 ± 4 | 2 |
| A3D1 | 55,523 | 55,490 ± 45 | 56,201 ± 13 | 711 ± 39 | 3 |
| A4 | 56,377 | 56,394 ± 8 | 57,378 ± 8 | 984 ± 7 | 4 |

Figure 3:
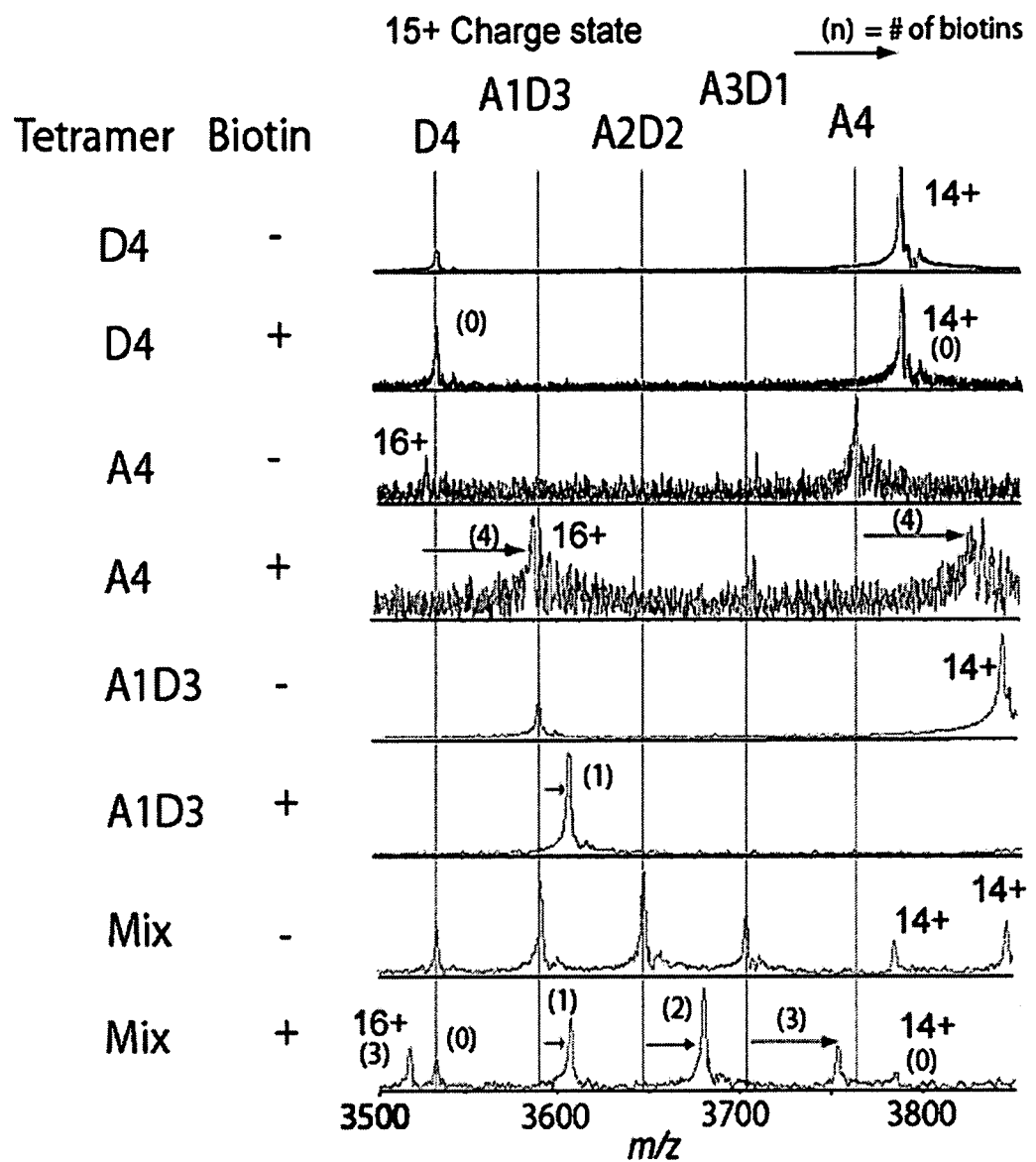
FIG. 3 shows spectra of representative data collected on mass spectrometry of chimeric streptavidins. Spectra are shown ±biotin for D4, A4, A1D3, and the initial product of refolding of D and A in a 3:1 ratio (Mix). Vertical lines indicate the predicted m/z for the 15+ charge state of the different tetramers without biotin. The 15+ charge state generally gave the sharpest peaks but the 14+ and 16+ peaks are also indicated. Horizontal arrows indicate the shift in m/z caused by binding of biotin. The number of biotin molecules bound is shown in parentheses.

Despite the large mass of the streptavidin tetramer and non-covalent interaction between subunits, good agreement was found between expected and observed masses for D4, A1D3, A2D2, A3D1 and A4 (Table 1 and FIG. 3).

Example 1

Figure 1B:
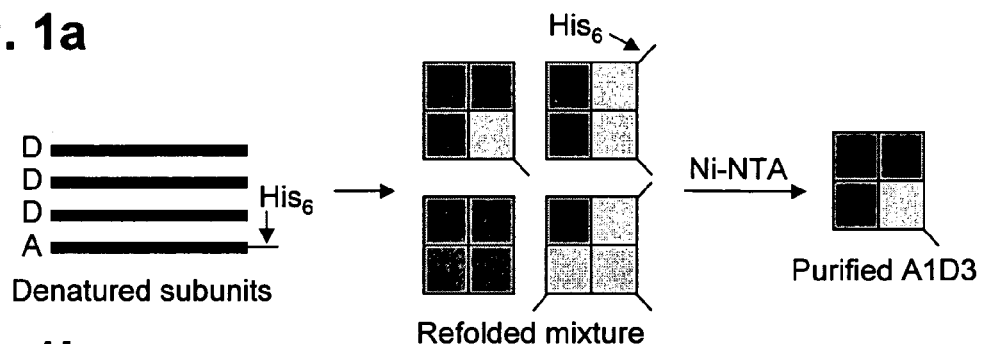
FIG. 1B is a schematic diagram depicting strategy for making monovalent streptavidin. Inactivated streptavidin subunits (D) and wild-type streptavidin subunits (A) in a 3:1 ratio were refolded from denaturant, giving a mix of streptavidin heterotetramers. Tetramers with a single $His_6$-tagged wild-type subunit were purified on a Ni-NTA column.
Figure 1C:
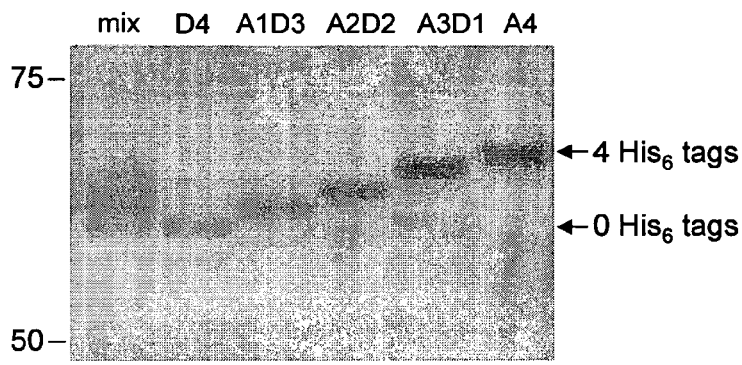
FIG. 1C is a digitized image of an SDS-PAGE gel of chimeric streptavidins under non-denaturing conditions. Streptavidin with 4 dead subunits (D4), wild-type streptavidin with a $His_6$-tag (A4), the initial product of refolding of D and A in a 3:1 ratio (mix), and chimeric tetramers with one (A1D3), two (A2D2), or three (A3D1) biotin binding subunits were loaded without boiling onto an 8% SDS-PAGE gel, and visualized by Coomassie staining.
Figure 1D:
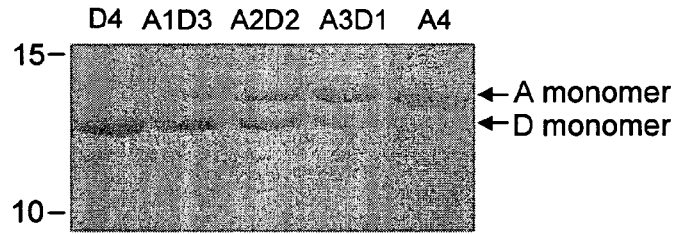
FIG. 1D shows a digitized image of an SDS-PAGE gel of chimeric streptavidins under denaturing conditions. Chimeric streptavidins with 0-4 A subunits were run as in FIG. 1C, except the samples were boiled before loading, to break the tetramer into constituent monomers. The changing ratio of A and D subunits can be seen.

The strategy used to generate monovalent streptavidin is shown is FIG. 1A. Methods provided in the Methods section above were used to make and test the monovalent streptavidin. We wished to produce a streptavidin tetramer consisting of three subunits unable to bind biotin and one subunit that binds biotin as well as wild-type streptavidin. Many of the known mutations of streptavidin reduce biotin binding affinity dramatically (Qureshi, M. H. et al., J Biol. Chem. 276: 46422-46428, 2001; Chilkoti, A. et al., Proc. Natl. Acad. Sci. USA 92: 1754-1758, 1995; Klumb, L. A. et al., Biochem. 37:

Example 2

Figure 2A:
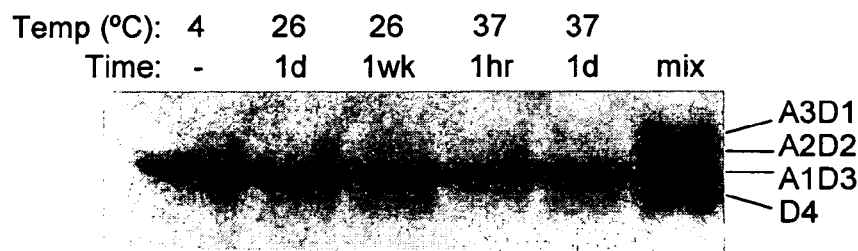
FIG. 2A shows a digitized image of an SDS-PAGE gel demonstrating the stability of monovalent streptavidin to subunit exchange. 5 μM A1D3 in PBS was incubated at 26° C. or 37° C. for 1 hour (hr), 1 day (d), or 1 week (wk) and rearranged tetramers were detected by 8% SDS-PAGE, by comparison to the initial product of refolding of D and A in a 3:1 ratio (mix).
Figure 2B:
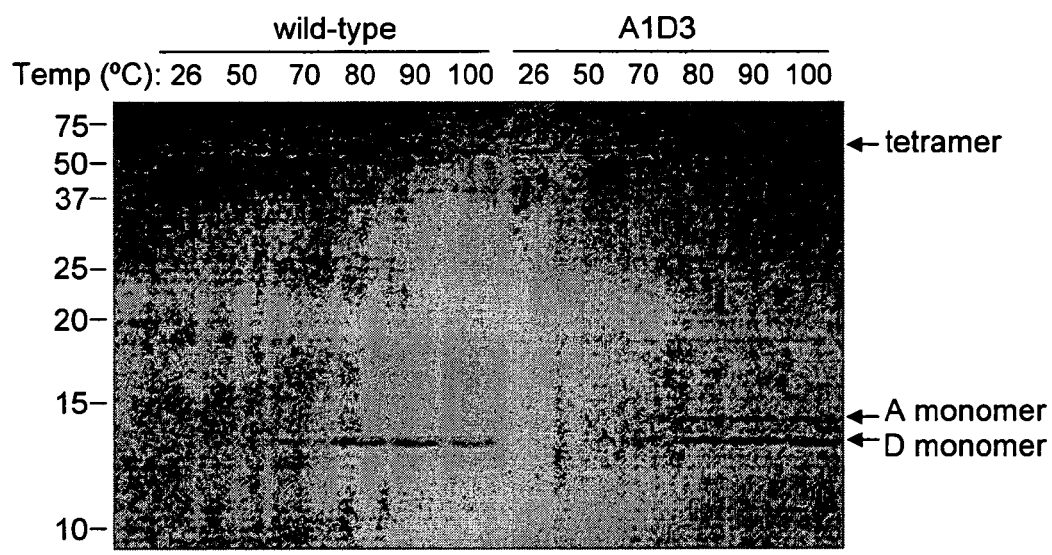
FIG. 2B shows an SDS-PAGE gel results indicating stability of tetramer to heat denaturation. 5 μM wild-type streptavidin or A1D3 in PBS was incubated at the indicated temperature (° C.) for 3 min and loaded onto a 16% SDS-PAGE gel.

Methods described in the Methods section above herein were used for the following production and testing of monovalent streptavidin. Tests were performed to determine whether monovalent streptavidin would rearrange its subunit composition over time. A1D3 was incubated at room temperature or at 37° C. and analyzed by SDS-PAGE, to look for the appearance of D4 and A2D2 from subunit exchange (FIG. 2A). 2% of the A1D3 rearranged into D4 after 37° C. incubation for one day and 3% rearranged after room temperature incubation for one week. Formation of A2D2 was not detected in either case, indicating that significant fractions of multivalent streptavidin will not be generated upon storage. Next the stability of A1D3 to dissociation into monomers was tested, since many mutations in the biotin binding site of streptavidin weaken tetramer stability (Qureshi, M. H. et al., J Biol. Chem. 276: 46422-46428, 2001; Wu, S. C. and Wong, S. L., J. Biol. Chem. 280: 23225-23231, 2005). Wild-type streptavidin and A1D3 were heated in PBS at various temperatures and tetramer disassembly was determined by SDS-PAGE (FIG. 2B). A significant fraction of A1D3 remained tetrameric even at 100° C. There was little difference in thermostability between wild-type and monovalent streptavidin, suggesting that the mutations in D have minimal effect on the subunit interfaces and that it should be possible to use A1D3 in assays requiring high temperatures.

Electrospray ionization mass spectrometry was used to characterize the number of biotin molecules bound per tetramer. Spectra of the different streptavidin tetramers with or without biotin were acquired. As expected, all four subunits of A4 were associated with biotin (Table 1 and FIG. 3). No biotin binding by D4 could be detected. A1D3 was monovalent, binding a single biotin. The other chimeric tetramers bound one biotin per A subunit.

Figure 4B:
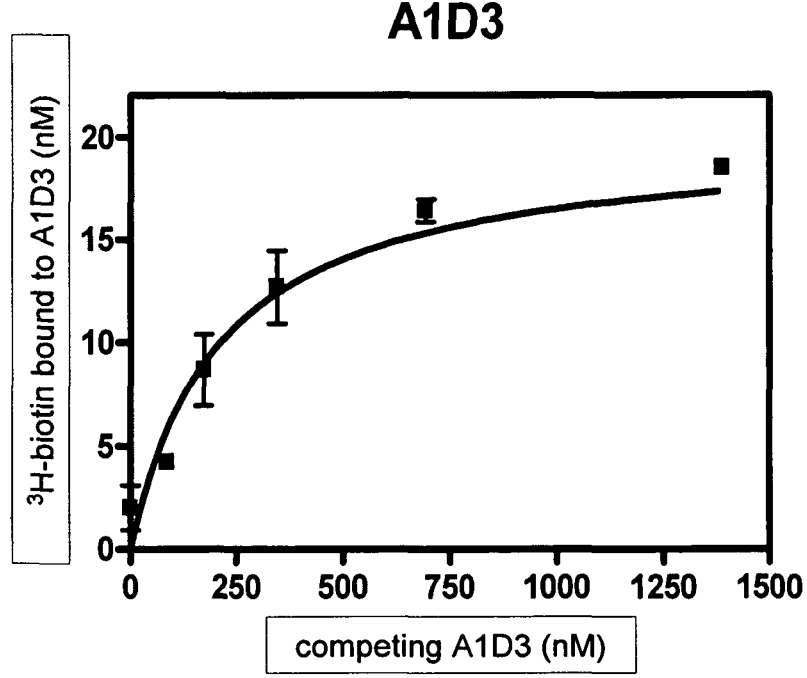
FIG. 4B shows the $K_d$ value determined for A1D3. For this determination increasing concentrations of A1D3 were incubated with 20 nM ³H-biotin and 60 nM wild-type streptavidin. After >20 hr, A1D3 was separated with Ni-NTA agarose, and the amount of ³H-biotin bound to wild-type streptavidin in the supernatant was measured. From this value, the amount of ³H-biotin bound to A1D3 was deduced. Means of triplicate measurement are shown ±1 s.d. Some error bars are too small to be visible. This gave a $K_d$ for A1D3 of 4.94±0.65×10⁻¹⁴M (s.e.m.).
Figure 5A:
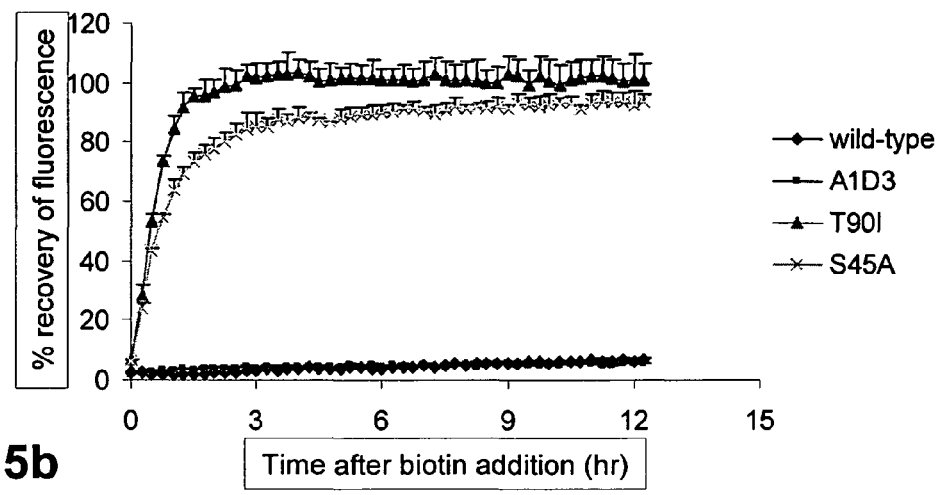
FIG. 5A shows comparative off-rates of Wild-type (♦), A1D3 (■), S45A (×) or T90I (▲) streptavidin, where each species was added in excess to biotin-4-fluorescein to quench its fluorescence. Excess competing biotin was added and fluorescence increase was monitored as biotin-4-fluorescein dissociated from streptavidin. 100% represents complete dissociation of biotin-4-fluorescein. Means of triplicate measurement are shown +1 s.d.
Figure 5B:
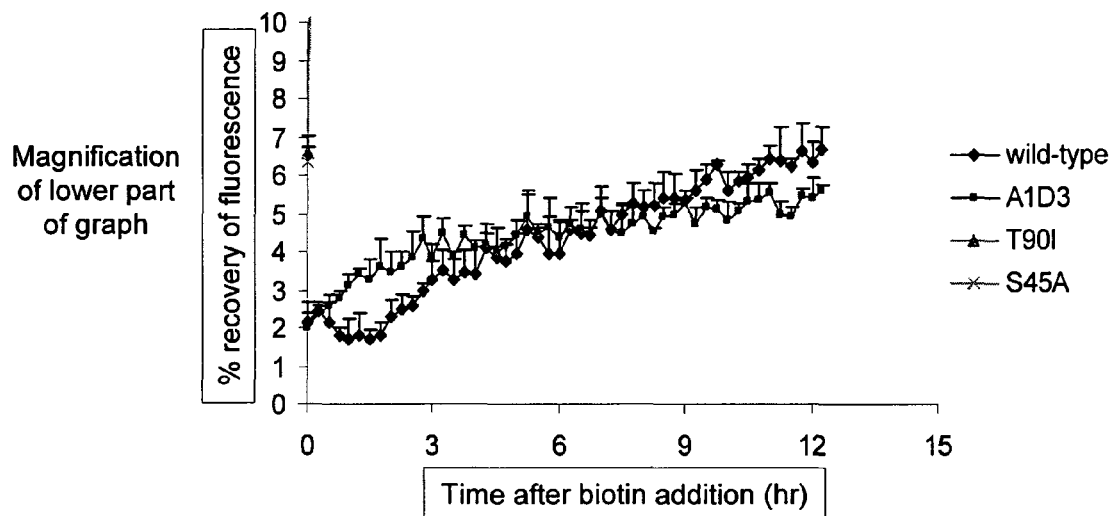
FIG. 5B shows a magnification of the 0-10% region of the y-axis from FIG. 5A, to illustrate the similar dissociation curves for wild-type streptavidin and A1D3.

The biotin binding affinity of A1D3 was determined by measuring competition with wild-type streptavidin for $^3$H biotin (Klumb, L. A. et al., Biochem. 37: 7657-7663, 1998) (FIG. 4B). This indicated that the active biotin binding site in A1D3 has an affinity of $4.9\pm0.7\times10^{-14}$M (s.e.m.), based on the affinity of wild-type streptavidin of $4.0\times10^{-14}$ M (Green, N. M. Methods in Enzymol. 184: 51-67, 1990). The stability of biotin-conjugate binding to A1D3 was also evaluated (FIG. 5). A previously characterized streptavidin mutant with a fast off-rate, S45A (Hyre, D. E. et al., Protein Sci. 9: 878-885, 2000), and a streptavidin mutant that was found to have a fast off-rate, T90I, were used as a positive control for biotin-conjugate dissociation. S45A and T90I streptavidin showed >50% dissociation in 1 hour, whereas wild-type and A1D3 both dissociated less than 10% in 12 hours at 37° C.

Figure 5C:
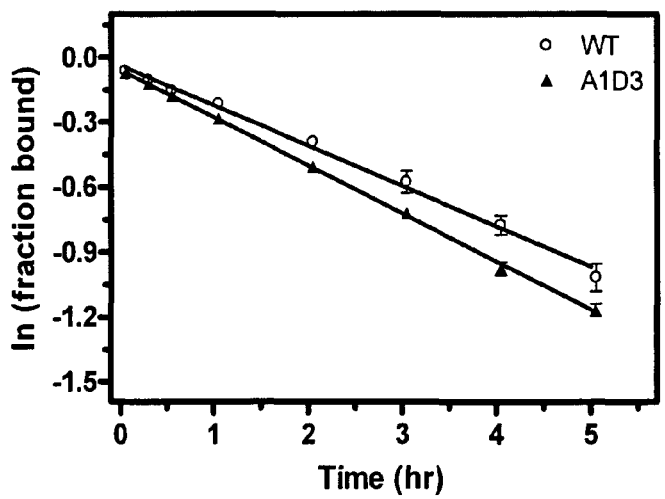
FIG. 5C shows results of a determination of off-rate of wild-type streptavidin (o) and A1D3 (▲) from biotin. A1D3 or wild-type streptavidin were incubated with ³H-biotin. Excess cold biotin was then added. After varying times at 37° C., the amount of bound ³H-biotin was determined by precipitating streptavidin. Means of triplicate measurement are shown ±1 s.d. The measured off-rates were 5.17±0.25×10⁻⁵ s⁻¹ (s.e.m.) for wild-type streptavidin and 6.14±0.19×10⁻⁵ s⁻¹ (s.e.m.) for A1D3.

To determine the off-rate of biotin from A1D3, 10 nM $^3$H-biotin was pre-incubated with 1 µM A1D3 or wild-type streptavidin for 20 minutes at 37° C. (Green, N. M. Methods in Enzymol. 184: 51-67, 1990). Dissociation was then initiated by addition of cold biotin at a final concentration of 50 µM and time-points taken over 5 hours at 37° C. 50 µL aliquots were removed and added to 200 µL 0.2M ZnSO$_4$ chilled on ice, followed by 200 µL 0.2 M NaOH. The protein precipitate was pelleted by centrifugation at 16,500 g for 5 min, and $^3$H-biotin in the supernatant was measured by liquid scintillation counting. Data were plotted as ln(fraction bound) versus time, and fit to a straight line by linear regression. Dissociation rates were deduced from the slope of the line and the equation:

$$\ln(\text{fraction bound})=-k_{off}(t)$$

where fraction bound=(total $^3$H-biotin–free $^3$H-biotin at timepoint)/(total $^3$H-biotin–free $^3$H-biotin before cold biotin chase). Results are shown in FIG. 5C. The measured off-rates were $5.17\pm0.25\times10^{-5}$s$^{-1}$ (s.e.m.) for wild-type streptavidin and $6.14\pm0.19\times10^{-5}$s$^{-1}$ (s.e.m.) for A1D3.

Site-specific biotinylation was used to study cell surface protein trafficking (Howarth, M. et al., Proc. Natl. Acad. Sci. USA 102: 7583-7588, 2005). Proteins of interest were tagged with a 15 amino acid acceptor peptide (AP), which was biotinylated by incubating cells with biotin ligase (BirA). The biotinylated protein was then tracked by labeling with fluorophore- or quantum dot-conjugated streptavidin (Howarth, M. et al., Proc. Natl. Acad. Sci. USA 102: 7583-7588, 2005), resulting in an interaction that was stable for many hours, unlike antibody labeling or other non-covalent site-specific labeling methods (Chen, I. and Ting, A. Y. Curr. Opin. Biotechnol. 16: 35-40, 2005).

Labeling of site-specifically biotinylated cell surface proteins with monovalent streptavidin was performed. Cyan fluorescent protein was tagged with AP and targeted to the surface of HeLa cells with a transmembrane domain (AP-CFP-TM). CFP-TM is cyan fluorescent protein with an acceptor peptide (AP), targeted to the cell surface with the transmembrane helix of PDGF receptor. HeLa expressing AP-CFP-TM or Ala-CFP-TM (a control with an alanine point mutation in AP) were biotinylated with biotin ligase for 10 min and stained with wild-type or monovalent (A1D3) streptavidin conjugated to Alexa Fluor 568. The Alexa-labeled and CFP-labeled images were overlaid. The results indicated no Alexa staining of AP-CFP-TM was observed when D4 was used or when biotin ligase was omitted and the cells were labeled with A1D3. Thus, after brief incubation with biotin ligase, biotinylated AP-CFP-TM was detected equally well with wild-type streptavidin or A1D3. However, an equivalent dye-conjugate of D4 gave no detectable staining, indicating that binding of A1D3 should only be through the A subunit. A point mutation in the acceptor peptide (Ala-CFP-TM) that blocked biotin ligase recognition abolished all staining. Staining was also abolished by omission of biotin ligase. Thus monovalent streptavidin did not give increased background in cell staining experiments compared to wild-type streptavidin.

Example 3

Cross-linking is a central method of control of signal transduction, for example in the activation of growth factor receptors and transcription factors (Klemm, J. D. et al., Annu. Rev. Immunol. 16: 569-592, 1998), but is a concern when labeling cells with antibodies. Although Fab antibody fragments could be used to avoid cross-linking, Fabs are rarely of high affinity (making it difficult to label low abundance antigens) and will tend to dissociate on the time-scale of minutes. Cross-linking is disastrous for single-particle tracking experiments because the presence of an extra anchor slows protein diffusion (Iino, R. et al., Biophys J. 80: 2667-2677, 2001). It is normally said that using a ligand in excess will minimize cross-linking. However, labeled ligand must be present at a density of <1 per µm$^2$ for individual particles to be resolved. Thus these two requirements are only compatible if one is studying a target protein present at very low levels. There is still a need for a way to label surface proteins with an interaction of high stability that does not cross-link.

Methods described in the Methods section above were used for the following neuroligin tests. Neuroligins are post-synaptic adhesion proteins that play a role in the development of excitatory and inhibitory synapses (Scheiffele, P. et al., Cell 101: 657-669, 2000; Levinson, J. N. et al., J. Biol. Chem. 280: 17312-17319, 2005). Clustering of neuroligin has been observed during synapse development, but neuroligin's role in synapse initiation versus synapse stabilization is not clear.

To examine the effect of artificially-induced neuroligin clustering, AP-neuroligin-1 was site-specifically biotinylated at the cell surface with biotin ligase, and detected with either wild-type or monovalent streptavidin. Hippocampal neurons were transfected with AP-neuroligin-1, biotinylated with biotin ligase, and labeled with Alexa Fluor 568-conjugated wild-type streptavidin or A1D3. Cells were incubated for 0 or 2 hr at 37° C. and Alexa staining was visualized by fluorescence microscopy. Neurons were biotinylated and labeled with wild-type streptavidin or A1D3 as above, but incubated for 24 hr and then stained for the pre-synaptic marker VGLUT1. Streptavidin and VGLUT1 signals were assessed and their images overlaid for comparison. It was determined that the AP-neuroligin-1 clusters were not apposed to pre-synaptic terminals. At zero hours, diffuse surface staining of AP-neuroligin-1 was observed with both wild-type and monovalent streptavidin. After a two hour incubation, however, monovalent streptavidin-labeled AP-neuroligin-1 was still predominantly diffuse [clusters/µm 0.087±0.021 (s.e.m), n=9], but wild-type streptavidin-labeled AP-neuroligin-1 had formed distinct aggregates [clusters/µm 0.266±0.011 (s.e.m), n=9, p<0.0001], consistent with tetramer-induced protein cross-linking. The same staining pattern was observed after 24 hour incubation.

The aggregation of AP-neuroligin-1 by wild-type streptavidin correlated with reduced formation of excitatory pre-synaptic contacts, determined by the intensity of vesicular glutamate transporter-1 clusters (VGLUT1) (fold-enhancement of VGLUT1 cluster intensity: wild-type 1.71±0.07, monovalent 2.15±0.12, n=17, p<0.01), and by the fact that many of the aggregates induced by wild-type streptavidin were not apposed by pre-synaptic terminals positive for VGLUT1. Thus induction of neuroligin clustering by wild-type streptavidin had a deleterious effect on pre-synaptic differentiation. The increase in VGLUT1 cluster intensity for neurons transfected with AP-neuroligin-1 and labeled with monovalent streptavidin was similar to the increase seen for HA-neuroligin-1 transfected neurons (Prange, O. et al., Proc. Natl. Acad. Sci. USA 101: 13915-13920, 2004), suggesting that AP, biotin, and monovalent streptavidin did not disrupt the function of neuroligin-1 or neuroligin-neurexin interactions. Taken together with previous observations (Levinson, J. N. et al., J. Biol. Chem. 280: 17312-17319, 2005; Graf, E. R. et al., Cell 119: 1013-1026, 2004), these results suggest that while gradual neuroligin clustering from DIV7 to DIV14 may promote pre-synaptic differentiation, rapid clustering does not. These results also indicate that monovalent streptavidin can efficiently label proteins on the neuron surface, while avoiding the complications of aggregation of its target.

Equivalents

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

---

We claim:

1. A stable monovalent streptavidin tetramer comprising three modified streptavidin monomer subunits and one wild-type streptavidin monomer subunit, wherein
   (i) the monovalent streptavidin tetramer has a single functional biotin binding site,
   (ii) the amino acid sequence of each modified streptavidin monomer subunit consists of the amino acid sequence set forth as SEQ ID NO: 3 with or without conservative amino acid substitutions.

2. The monovalent streptavidin tetramer of claim 1, wherein the wild-type streptavidin monomer subunit binds biotin with a $K_d$ of a wild-type streptavidin monomer subunit for binding biotin.

3. The monovalent streptavidin tetramer of claim 1, wherein the monovalent streptavidin tetramer has a proximal streptavidin $K_d$ for binding biotin.

4. The monovalent streptavidin tetramer of claim 1, wherein the single functional biotin binding site is a femtomolar biotin binding site.

5. The monovalent streptavidin tetramer of claim 1, wherein the monovalent streptavidin tetramer has a proximal streptavidin overall biotin off-rate.

6. The monovalent streptavidin tetramer of claim 1, wherein the substituted amino acid residues are in the sequence of a biotin binding pocket of the streptavidin monomer subunit.

7. The monovalent streptavidin tetramer of claim 1, wherein one or more of the modified or wild-type streptavidin monomer subunits further comprises a purification tag.

8. The monovalent streptavidin tetramer of claim 7, wherein the purification tag is a polyhistidine tag.

9. The monovalent streptavidin tetramer of claim 7, wherein the streptavidin monomer subunit further comprising the purification tag is the wild-type streptavidin monomer subunit.

10. The monovalent streptavidin tetramer of claim 1, further comprising a detectable label.

11. The monovalent streptavidin tetramer of claim 1, wherein the monovalent streptavidin tetramer is made by mixing together streptavidin monomers under conditions in which the monomers associate into tetramers.

12. A method of making a plurality of stable monovalent streptavidin tetramers, comprising mixing together wild-type and modified streptavidin monomers under conditions in which the streptavidin monomers associate into stable monovalent streptavidin tetramers, wherein the monovalent streptavidin tetramers are formed by associating one wild-type streptavidin monomer subunit and three modified streptavidin monomer subunits, wherein the monovalent streptavidin tetramers each have a single functional biotin binding site and one or more of the following characteristics:
   (a) a proximal streptavidin $K_d$ for binding biotin,
   (b) the single functional biotin binding site is a femtomolar biotin binding site,
   (c) a proximal streptavidin overall biotin off-rate, wherein the modified streptavidin monomer subunit consists of the amino acid sequence set forth as SEQ ID NO: 3 with or without conservative amino acid substitutions.

13. A method of binding biotin comprising:
   contacting a biological sample comprising biotin with a monovalent streptavidin tetramer of claim 1 under conditions that permit binding of biotin with a monovalent streptavidin tetramer.

14. A method for labeling a protein without causing significant protein aggregation, said method comprising contacting a biological sample comprising biotin with a stable monovalent streptavidin tetramer having three modified streptavidin monomer subunits and one wild-type streptavidin monomer subunit under conditions that permit binding of biotin with the stable monovalent streptavidin tetramer, wherein
   (i) the monovalent streptavidin tetramer has a single functional biotin binding site, and
   (ii) the amino acid sequence of each modified streptavidin monomer subunit consists of the amino acid sequence set forth as SEQ ID NO: 3 with or without conservative amino acid substitutions.

* * * * *

UNITED STATES PATENT AND TRADEMARK OFFICE
CERTIFICATE OF CORRECTION

PATENT NO. : 8,586,708 B2
APPLICATION NO. : 11/262325
DATED : November 19, 2013
INVENTOR(S) : Ting et al.

It is certified that error appears in the above-identified patent and that said Letters Patent is hereby corrected as shown below:

In The Specification

Column 1, lines 6-9, delete

"This invention was made in part with government support under grant number P20GM072029-01 from the National Institutes of Health (NIH). The United States Government may have certain rights in this invention."

and replace with:

"This invention was made with Government support under Grant No. P20 GM072029 awarded by the National Institutes of Health. The Government has certain rights in the invention."

Signed and Sealed this
Nineteenth Day of April, 2016

Michelle K. Lee
*Director of the United States Patent and Trademark Office*